United States Patent [19]
Henry et al.

[11] Patent Number: 5,529,912
[45] Date of Patent: Jun. 25, 1996

[54] INOSITOL-EXCRETING YEAST

[75] Inventors: Susan A. Henry; Michael J. White, both of Pittsburgh, Pa.

[73] Assignee: Carnegie Mellon University, Pittsburgh, Pa.

[21] Appl. No.: 453,477

[22] Filed: May 30, 1995

Related U.S. Application Data

[63] Continuation of Ser. No. 672,355, Mar. 20, 1991, abandoned.

[51] Int. Cl.$^6$ .................................. C12P 7/02; C12P 7/64; C12N 9/12; C12N 1/19
[52] U.S. Cl. ................ 435/155; 435/172.1; 435/172.3; 435/134; 435/194; 435/254.2; 435/254.21; 435/320.1; 536/23.1; 536/23.2; 536/23.7
[58] Field of Search ............................. 435/172.1, 172.3, 435/326.1, 155, 194, 134, 254.2, 254.21; 536/23.1, 23.2, 23.7

[56] References Cited

PUBLICATIONS

Sanger et al. PNAS 74:5463 (1977).
Orr–Weaver et al. Mol. Cell. Biol. 3:747 (1983).
Torchia et al. Mol. Cell. Biol. 4:1521 (1984).
Boeka et al. Science 239:280 (1988).
Klig et al. J. Bact 162:1135 (1985).
Hirsch et al. Genet. 116, Suppl. No. 1, pt. 2:551, abstract B.21 (1987).
Hirsch et al. Mol. Cell. Biol. 6:3320 (1986).

*Primary Examiner*—John L. LeGuyader
*Attorney, Agent, or Firm*—Reed Smith Shaw & McClay

[57] ABSTRACT

A yeast cell, preferably *Saccharomyces cerevisiae*, which contains a functional stable recombinant DNA sequence that does not allow for the encoding of a negative regulator of phospholipid biosynthesis therein and which has multiple copies of an INO1 gene. In a preferred embodiment, the recombinant DNA sequence is an OPI1 gene deletion which results in the deregulation of inositol or inositol-containing metabolites such as inositol-1-phosphate synthase. Moreover, there is a method for obtaining inositol, inositol-containing metabolites or phospholipids such as myo-inositol or inositol-1-phosphate. The method comprises the steps of genetically engineering a stable yeast cell, preferably *Saccharomyces cerevisiae*, to continually produce inositol, inositol-containing metabolites or phospholipids. Additionally, there is the step of then generating the inositol, inositol-containing metabolites or phospholipids. In a preferred embodiment, the genetically engineering step includes the step of altering the negative regulatory step involved in phospholipid biosynthesis to overproduce inositol, inositol-containing metabolites or phospholipids such as myo-inositol.

16 Claims, 15 Drawing Sheets

FIG. 8a

```
        10         20         30         40         50         60         70
CTCGAGATAA GTTGGTCAAC ATTGATTTCG AGATTCCGTA CTGTACATGC AGTGGCCTGA AAGTTGAGTA
        80         90        100        110        120        130
CTTGAAGGTC GAAGAGCCAC AATTGCAGTA CCAGTCTTTC CCCTGGGTCA GATACAAGAC
       140        150        160        170        180        190
CGTCAGCGAC GAAGAGTACG CATATATTGT TTGACGCTTA CGCAGACATC TCATAGATAG
       200        210        220        230        240        250
ACAAATGGTA CGTTCGTTTT AGTATATAGA TGGCACCTTA TAATCTTCAT ATGCAACCGG
       260        270        280        290        300        310
GTAAAATCGG GCGTTCTTAT TTTTTTTTTT TCCACCTCAA TGAGAGGGAT TAATAAGAGG
       320        330        340        350        360        370
ATTGGAGCAA GACAGCGATC TGCACTTAGC CAAGAAAGCA TATCAGGCCA GAACGTGGCA
       380        390        400        410        420        430
TTTTGTTTAC AGTGCTGATT AAAGCGTGTG TATCAGGACA GTGTTTTTAA CGAAGATACT
```

```
                                     Met Ser Glu Asn Gln Arg Leu Gly Leu Ser Glu Glu Val Glu Ala
AGTCATTG ATG TCT GAA AAT CAA CGT TTA GGA TTA TCA GAG GAA GTA GAA GCG
         441                         450                 459             468             477         486

Ala Glu Val Leu Gly Val Leu Lys Gln Ser Cys Arg Gln Lys Ser Gln Pro Ser
GCT GAA GTA CTT GGG GTG TTG AAA CAA TCA TGC AGA CAG AAG TCG CAG CCT TCA
        495                 504             513             522             531         540

Glu Asp Val Ser Gln Ala Asp Lys  Met  Pro Ala Ser Glu Ser Ser Thr Thr Pro
GAG GAC GTC TCA CAA GCT GAC AAA  ATG  CCG GCA AGT GAG TCG TCT ACG ACG CCG
        549                 558             567             576             585         594

Leu Asn Ile Leu Asp Arg Val Ser Asn Lys Ile Ile Ser Asn Val Val Thr Phe
CTA AAC ATT TTG GAT CGC GTA AGT AAC AAA ATT ATC AGT AAC GTA GTG ACA TTC
        603                 612             621             630             639         648

Tyr Asp Glu Ile Asn Thr Asn Lys Arg Pro Leu Lys Ser Ile Gly Arg Leu Leu
TAC GAT GAA ATA AAC ACC AAC AAG AGG CCA CTG AAA TCA ATA GGG AGG CTG CTA
        657                 666             675             684             693         702
```

FIG.8b

```
Asp Asp Asp Asp Glu His Asp Asp Tyr Asn Asp Glu Phe Phe
GAC GAT GAC GAT GAG CAT GAT GAT TAC AAC GAC GAG TTC TTC
711              720              729              738              747              756

Thr Asn Lys Arg Gln Lys Leu Ser Arg Ala Ile Ala Lys Gly Lys Asp Asn Leu
ACC AAC AAG AGA CAG AAG CTG TCG CGG GCG ATT GCC AAG GGG AAG GAC AAC TTG
765              774              783              792              801              810

Lys Glu Tyr Lys Leu Asn Met Ser Ile Glu Ser Lys Lys Arg Leu Val Thr Cys
AAA GAG TAC AAG CTG AAC ATG TCC ATC GAG TCT AAG AAG AGG CTT GTA ACG TGC
819              828              837              846              855              864

Leu His Leu Leu Lys Leu Lys Gln Leu Ala Asn Lys Gln Leu Ser Asp Lys Ile Ser Cys Leu
TTG CAT CTT TTA AAG CTT AAG CTG GCC AAT AAG CAG CTT TCC GAT AAA ATC TCG TGT TTA
873              882              891              900              909              918

Gln Asp Leu Val Glu Lys Glu Gln Val His Pro Leu His Lys Gln Asp Gly Asn
CAG GAC CTT GTT GAA AAG GAG CAG GTG CAT CCT TTG CAC AAG CAA GAT GGA AAT
927              936              945              954              963              972
```

FIG.8c

```
Ala Arg Thr Thr Gly Ala Gly Glu Asp Thr Ser Ser Asp Glu Asp Asp
GCT AGG ACG ACC GGA GCT GGC GAG GAC ACA TCG TCA GAC GAA GAC GAC
981                     990                     999                    1008                    1017                    1026

Asp Asp Glu Glu Phe Phe Asp Ala Ser Glu Gln Val Asn Ala Ser Glu Gln Ser
GAC GAT GAG GAG TTT TTT GAT GCC TCA GAG CAG GTC AAC GCC AGC GAG CAG TCT
1035                    1044                    1053                    1062                    1071                    1080

Ile Val Val Lys [Met] Glu Val Val Gly Thr Val Lys Lys Val Tyr Ser Leu Ile
ATT GTG GTG AAA [ATG] GAG GTG GTC GGC ACA GTC AAG AAA GTC TAC TCG CTG ATA
1089                    1098                    1107                    1116                    1125                    1134

Ser Lys Phe Thr Ala Asn Ser Leu Pro Glu Pro Ala Arg Ser Gln Val Arg Glu
TCG AAG TTC ACA GCA AAT TCG CTG CCG GAG CCC GCA AGA TCT CAG GTT CGG GAA
1143                    1152                    1161                    1170                    1179                    1188

Ser Leu Leu Asn Leu Pro Thr Asn Trp Phe Asp Ser Val His Ser Thr Ser Leu
AGT CTT CTA AAC CCC ACA AAT TGG TTC GAC AGC AGT CAC AGT ACA TCA CTG
1197                    1206                    1215                    1224                    1233                    1242
                                                                                                                         *
Pro His His Ala Ser Phe His Tyr Ala Asn Cys Glu Gln Lys Val Gln [Gln]
CCG CAT CAT GCT TCG TTT CAT TAT GCC AAC TGT GAA CAA AAA GTG GAG CAA
1251                    1260                    1269                    1278                    1287                    1296
```

FIG. 8d

| Gln | Gln | Gln | Gln | Gln | Gln | Gln | Gln | Gln | Gln | Gln | Gln | Gln | Leu |
|---|---|---|---|---|---|---|---|---|---|---|---|---|---|
| CAG | CAA | CAG | CAA | CAG | CAG | CAG | CAG | CAA | CTT | TTG | CAG | CAA | CTC |
| 1305 | | | 1314 | | | 1323 | | | 1332 | | | 1341 | 1350 |

| Leu | Gln | Gln | Gln | Gln | Lys | Arg | Asn | Lys | Asp | Gly | Asp | Asp | Ser | Ala | Ser | Pro |
|---|---|---|---|---|---|---|---|---|---|---|---|---|---|---|---|---|
| CTG | CAA | CAG | CAA | CAA | AAA | AGG | AAC | AAG | GAT | GGC | GAC | GAC | TCA | GCC | TCG | CCG |
| 1359 | | | 1368 | | | 1377 | | | 1386 | | | 1395 | | | 1404 | |

| Ser | Ser | Ser | Val | Thr | Ala | Asn | Gly | Lys | Val | Leu | Ile | Leu | Ala | Lys | Glu | Ser | Leu |
|---|---|---|---|---|---|---|---|---|---|---|---|---|---|---|---|---|---|
| TCC | TCC | TCC | GTA | ACT | GCG | AAT | GGG | AAA | GTA | CTC | ATT | CTC | GCC | AAA | GAA | TCC | CTG |
| 1413 | | | 1422 | | | 1431 | | | 1440 | | | 1449 | | | 1458 | |

| Glu | Met | Val | Arg | Asn | Val | Met | Gly | Val | Val | Asp | Ser | Thr | Leu | Gly | Lys | Ala | Glu |
|---|---|---|---|---|---|---|---|---|---|---|---|---|---|---|---|---|---|
| GAA | ATG | GTG | AGA | AAT | GTC | ATG | GGC | GTA | GTC | GAC | TCC | ACG | TTG | GGC | AAG | GCT | GAA |
| 1467 | | | 1476 | | | 1485 | | | 1494 | | | 1503 | | | 1512 | |

| Glu | Trp | Val | Lys | Gln | Lys | Gln | Glu | Val | Lys | Glu | Met | Ile | Arg | Glu | Arg | Phe | Leu |
|---|---|---|---|---|---|---|---|---|---|---|---|---|---|---|---|---|---|
| GAA | TGG | GTG | AAG | CAG | AAA | CAG | GAG | GTA | AAA | GAG | ATG | ATC | AGG | GAG | CGT | TTC | TTG |
| 1521 | | | 1530 | | | 1539 | | | 1548 | | | 1557 | | | 1566 | |

FIG. 8e

| Gln | Gln | Gln | Gln | Gln | Tyr | Arg | Gln | Gln | Gln | Gln | Lys | Asp | Gly | Asn | Tyr | Val | Lys |
|---|---|---|---|---|---|---|---|---|---|---|---|---|---|---|---|---|---|
| CAA | CAG | CAG | CAG | CAA | TAC | AGG | CAG | CAA | CAG | CAG | AAG | GAT | GGC | AAT | TAC | GTA | AAG |
| 1575 | | | 1584 | | | 1593 | | | 1602 | | | 1611 | | | | | 1620 |

Pro Ser Gln Asp Asn Val Asp Ser Lys Asp  
CCC TCT CAG GAC AAC GTG GAT AGC AAG GAC TAA CCGAGAC AGATTGAGGT  
1629          1638          1647                    1660          1670

```
         1680       1690       1700       1710       1720       1730
CTTTCATGCA TTACCACCAG TAATAATATT ATACGGAATA ATATAGTTTA TATAATATCC
         1740       1750       1760       1770       1780       1790
ATAATCATAA TCATAATCAT AATCATAAATC ATAATCGTGA TATTGTACCA GCCCCGCTTC
         1800       1810       1820       1830       1840       1850
TCCCCTTTTG AACTACCATT ATTATCGGAC CCTCTTTACC TTTGAATGGC TCAGTAAGGA
         1860       1870       1880       1890
CCTTTGCGCG CCGTAAGGGG GTCGGGAATA CATTCCGGGG GTTGATC
```

FIG. 8f

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1897 base pairs
        ( B ) TYPE: nucleic acid ( C ) STRANDEDNESS: double
( D ) TOPOLOGY: linear ( i i ) MOLECULE TYPE:
( A ) DESCRIPTION: Genomic DNA with translated open-reading
frame containing the putative Opi1 protein ( i i i ) HYPOTHETICAL: No ( i v ) ANTI-SENSE: No ( v i ) ORIGINAL SOURCE:
( A ) ORGANISM: Saccharomyces cerevisiae
( B ) STRAIN: Generic laboratory strain ( v i i ) IMMEDIATE SOURCE:
( A ) LIBRARY: YCp19 Library
( B ) CLONE: p(SPO11)1

( v i i i ) POSITION IN GENOME:
( A ) CHROMOSOME/SEGMENT: Chromosome VIII
( B ) MAP POSITION: Adjacent to SPO11

( i x ) FEATURE:
( A ) NAME/KEY: OPI1 Gene
( B ) LOCATION: GenBankTM/EMBL Data Bank. Accession
number J05727
( C ) IDENTIFICATION METHOD: OPI1 gene was cloned using the
SPO11 mapping technique. The cloned gene complemented an
opi1 mutant strain.
( D ) OTHER INFORMATION: The cloned OPI1 gene restored INO1
regulation in an opi1 mutant strain resulting in the loss
of overproduction of inositol.

( x ) PUBLICATION INFORMATION:
( A ) AUTHORS: Michael J. White
Jeanne P. Hirsch
Susan A. Henry
( B ) TITLE: The OPI1 Gene of Saccharomyces cerevisiae, a
Negative Regulator of Phospholipid Biosynthesis,
Encodes a Protein Containing Polyglutamine
Tracts and a Leucine Zipper
( C ) JOURNAL: The Journal of Biological Chemistry
( D ) VOLUME: 266
( E ) ISSUE: 2
( F ) PAGES: 863-872
( G ) DATE: 15-1-91

( x i ) SEQUENCE DESCRIPTION: SEQ ID NO: 1:

```
                CTCGAGAT  AAGTTGGTCA  ACATTGATTT  CGAGATTCCG                        38

TACTGTACAT  GCAGTGGCCT  GAAAGTTGAG  TACTTGAAGG  TCGAAGAGCC                        88

ACAATTGCAG  TACCAGTCTT  TCCCCTGGGT  CAGATACAAG  ACCGTCAGCG                       138

ACGAAGAGTA  CGCATATATT  GTTTGACGCT  TACGCAGACA  TCTCATAGAT                       188

AGACAAATGG  TACGTTCGTT  TTAGTATATA  GATGGCACCT  TATAATCTTC                       238

ATATGCAACC  GGGTAAAATC  GGGCGTTCTT  ATTTTTTTTT  TTTCCACCTC                       288

AATGAGAGGG  ATTAATAAGA  GGATTGGAGC  AAGACAGCGA  TCTGCACTTA                       338

GCCAAGAAAG  CATATCAGGC  CAGAACGTGG  CATTTTGTTT  ACAGTGCTGA                       388

TTAAAGCGTG  TGTATCAGGA  CAGTGTTTTT  AACGAAGATA  CTAGTCATTG                       438

ATG  TCT  GAA  AAT  CAA  CGT  TTA  GGA  TTA  TCA  GAG  GAA  GAG  GTA  GAA       483
Met  Ser  Glu  Asn  Gln  Arg  Leu  Gly  Leu  Ser  Glu  Glu  Glu  Val  Glu
               0 5                    1 0                        1 5

GCG  GCT  GAA  GTA  CTT  GGG  GTG  TTG  AAA  CAA  TCA  TGC  AGA  CAG  AAG       528
Ala  Ala  Glu  Val  Leu  Gly  Val  Leu  Lys  Gln  Ser  Cys  Arg  Gln  Lys
               2 0                    2 5                        3 0

TCG  CAG  CCT  TCA  GAG  GAC  GTC  TCA  CAA  GCT  GAC  AAA  ATG  CCG  GCA       573
Ser  Gln  Pro  Ser  Glu  Asp  Val  Ser  Gln  Ala  Asp  Lys  Met  Pro  Ala
               3 5                    4 0                        4 5
```

| | | | | | | | | | | | | | | |
|---|---|---|---|---|---|---|---|---|---|---|---|---|---|---|
| AGT | GAG | TCG | TCT | ACG | ACG | CCG | CTA | AAC | ATT | TTG | GAT | CGC | GTA | AGT | 618
| Ser | Glu | Ser | Ser | Thr 50 | Thr | Pro | Leu | Asn | Ile 55 | Leu | Asp | Arg | Val | Ser 60
| AAC | AAA | ATT | ATC | AGT | AAC | GTA | GTG | ACA | TTC | TAC | GAT | GAA | ATA | AAC | 663
| Asn | Lys | Ile | Ile | Ser 65 | Asn | Val | Val | Thr | Phe 70 | Tyr | Asp | Glu | Ile | Asn 75
| ACC | AAC | AAG | AGG | CCA | CTG | AAA | TCA | ATA | GGG | AGG | CTG | CTA | GAC | GAT | 708
| Thr | Asn | Lys | Arg | Pro 80 | Leu | Lys | Ser | Ile | Gly 85 | Arg | Leu | Leu | Asp | Asp 90
| GAC | GAT | GAC | GAG | CAT | GAT | GAT | TAC | GAC | TAC | AAC | GAC | GAT | GAG | TTC | 753
| Asp | Asp | Asp | Glu | His 95 | Asp | Asp | Tyr | Asp | Tyr 100 | Asn | Asp | Asp | Glu | Phe 105
| TTC | ACC | AAC | AAG | AGA | CAG | AAG | CTG | TCG | CGG | GCG | ATT | GCC | AAG | GGG | 798
| Phe | Thr | Asn | Lys | Arg 110 | Gln | Lys | Leu | Ser | Arg 115 | Ala | Ile | Ala | Lys | Gly 120
| AAG | GAC | AAC | TTG | AAA | GAG | TAC | AAG | CTG | AAC | ATG | TCC | ATC | GAG | TCT | 843
| Lys | Asp | Asn | Leu | Lys 125 | Glu | Tyr | Lys | Leu | Asn 130 | Met | Ser | Ile | Glu | Ser 135
| AAG | AAG | AGG | CTT | GTA | ACG | TGC | TTG | CAT | CTT | TTA | AAG | CTG | GCC | AAT | 888
| Lys | Lys | Arg | Leu | Val 140 | Thr | Cys | Leu | His | Leu 145 | Leu | Lys | Leu | Ala | Asn 150
| AAG | CAG | CTT | TCC | GAT | AAA | ATC | TCG | TGT | TTA | CAG | GAC | CTT | GTT | GAA | 933
| Lys | Gln | Leu | Ser | Asp 155 | Lys | Ile | Ser | Cys | Leu 160 | Gln | Asp | Leu | Val | Glu 165
| AAG | GAG | CAG | GTG | CAT | CCT | TTG | CAC | AAG | CAA | GAT | GGA | AAT | GCT | AGG | 978
| Lys | Glu | Gln | Val | His 170 | Pro | Leu | His | Lys | Gln 175 | Asp | Gly | Asn | Ala | Arg 180
| ACG | ACC | ACT | GGA | GCT | GGC | GAG | GAC | GAG | ACA | TCG | TCA | GAC | GAA | GAC | 1023
| Thr | Thr | Thr | Gly | Ala 185 | Gly | Glu | Asp | Glu | Thr 190 | Ser | Ser | Asp | Glu | Asp 195
| GAC | GAC | GAT | GAG | GAG | TTT | TTT | GAT | GCC | TCA | GAG | CAG | GTC | AAC | GCC | 1068
| Asp | Asp | Asp | Glu | Glu 200 | Phe | Phe | Asp | Ala | Ser 205 | Glu | Gln | Val | Asn | Ala 210
| AGC | GAG | CAG | TCT | ATT | GTG | GTG | AAA | ATG | GAG | GTG | GTC | GGC | ACA | GTC | 1113
| Ser | Glu | Gln | Ser | Ile 215 | Val | Val | Lys | Met | Glu 220 | Val | Val | Gly | Thr | Val 225
| AAG | AAA | GTC | TAC | TCG | CTG | ATA | TCG | AAG | TTC | ACA | GCA | AAT | TCG | CTG | 1158
| Lys | Lys | Val | Tyr | Ser 230 | Leu | Ile | Ser | Lys | Phe 235 | Thr | Ala | Asn | Ser | Leu 240
| CCG | GAG | CCC | GCA | AGA | TCT | CAG | GTT | CGG | GAA | AGT | CTT | CTA | AAC | TTA | 1203
| Pro | Glu | Pro | Ala | Arg 245 | Ser | Gln | Val | Arg | Glu 250 | Ser | Leu | Leu | Asn | Leu 255
| CCC | ACA | AAT | TGG | TTC | GAC | AGC | GTC | CAC | AGT | ACA | TCA | CTG | CCG | CAT | 1248
| Pro | Thr | Asn | Trp | Phe 260 | Asp | Ser | Val | His | Ser 265 | Thr | Ser | Leu | Pro | His 270
| CAT | GCT | TCG | TTT | CAT | TAT | GCC | AAC | TGT | GAA | GAA | CAA | AAA | GTG | GAG | 1293
| His | Ala | Ser | Phe | His 275 | Tyr | Ala | Asn | Cys | Glu 280 | Glu | Gln | Lys | Val | Gln 285
| CAA | CAG | CAA | CAG | CAA | CAG | CAA | CAG | CAG | CAG | CAG | CAA | CTT | TTG | | 1338
| Gln | Gln | Gln | Gln | Gln 290 | Gln | Gln | Gln | Gln | Gln 295 | Gln | Gln | Leu | Leu 300 | |
| CAG | CAG | CAA | CTC | CTG | CAA | CAG | CAA | CAG | CAA | AAA | AGG | AAC | AAG | GAT | 1383
| Gln | Gln | Gln | Leu | Leu 305 | Gln | Gln | Gln | Gln | Gln 310 | Lys | Arg | Asn | Lys | Asp 315
| GGC | GAC | GAC | TCA | GCC | TCG | CCG | TCC | TCC | TCC | GTA | ACT | GCG | AAT | GGG | 1428
| Gly | Asp | Asp | Ser | Ala 320 | Ser | Pro | Ser | Ser | Ser 325 | Val | Thr | Ala | Asn | Gly 330
| AAA | GTA | CTC | ATT | CTC | GCC | AAA | GAA | TCC | CTG | GAA | ATG | GTG | AGA | AAT | 1473
| Lys | Val | Leu | Ile | Leu 335 | Ala | Lys | Glu | Ser | Leu 340 | Glu | Met | Val | Arg | Asn 345

| | | | | | | | | | | | | | | |
|---|---|---|---|---|---|---|---|---|---|---|---|---|---|---|
| GTC | ATG | GGC | GTA | GTC | GAC | TCC | ACG | TTG | GGC | AAG | GCT | GAA | GAA | TGG | 1518
| Val | Met | Gly | Val | Val | Asp | Ser | Thr | Leu | Gly | Lys | Ala | Glu | Glu | Trp |
| | | | | 350 | | | | | 355 | | | | | 360 |
| GTG | AAG | CAG | AAA | CAG | GAG | GTA | AAA | GAA | ATG | ATC | AGG | GAG | CGT | TTC | 1563
| Val | Lys | Gln | Lys | Gln | Glu | Val | Lys | Glu | Met | Ile | Arg | Glu | Arg | Phe |
| | | | | 365 | | | | | 370 | | | | | 375 |
| TTG | CAA | CAG | CAG | CAA | CAG | TAC | AGG | CAG | CAA | CAG | CAG | AAG | GAT | GGC | 1608
| Leu | Gln | Gln | Gln | Gln | Gln | Tyr | Arg | Gln | Gln | Gln | Gln | Lys | Asp | Gly |
| | | | | 380 | | | | | 385 | | | | | 390 |
| AAT | TAC | GTA | AAG | CCC | TCT | CAG | GAC | AAC | GTG | GAT | AGC | AAG | GAC | TAA | 1653
| Asn | Tyr | Val | Lys | Pro | Ser | Gln | Asp | Asn | Val | Asp | Ser | Lys | Asp | |
| | | | | 395 | | | | | 400 | | | | | |

```
CCGAGACAGA  TTGAGGTCTT  TCATGCATTA  CCACCAGTAA  TAATATTATA          1703

CGGAATAATA  TAGTTTATAT  AATATCCATA  ATCATAATCA  TAATCATAAT          1753

CATAATCATA  ATCGTGATAT  TGTACCAGCC  CCGCTTCTCC  CCTTTTGAAC          1803

TACCATTATT  ATCGGACCCT  CTTTACCTTT  GAATGGCTCA  GTAAGGACCT          1853

TTGCGCGCCG  TAAGGGGGTC  GGGAATACAT  TTCCGGGGTT  GATC                1897
```

( 2 ) INFORMATION FOR SEQ ID NO:2:

( i ) SEQUENCE CHARACTERISTICS:
        ( A ) LENGTH: 404 amino acids
        ( B ) TYPE: amino acid
        ( D ) TOPOLOGY: linear ( i i ) MOLECULE TYPE: Protein ( i i i ) HYPOTHETICAL: Yes ( x ) PUBLICATION INFORMATION:
        ( A ) AUTHORS: Michael J. White
                  Jeanne P. Hirsch
                  Susan A. Henry
        ( B ) TITLE: The OPI1 Gene of Saccharomyces cerevisiae, a
               Negative Regulator of Phospholipid Biosynthesis,
               Encodes a Protein Containing Polyglutamine
               Tracts and a Leucine Zipper
        ( C ) JOURNAL: The Journal of Biological Chemistry
        ( D ) VOLUME: 266
        ( E ) ISSUE: 2
        ( F ) PAGES: 863-872
        ( G ) DATE: 15-JAN-91

( x i ) SEQUENCE DESCRIPTION: SEQ ID NO: 2:

| Met | Ser | Glu | Asn | Gln | Arg | Leu | Gly | Leu | Ser | Glu | Glu | Val | Glu |
|---|---|---|---|---|---|---|---|---|---|---|---|---|---|
| 1 | | | | 5 | | | | | 10 | | | | 15 |
| Ala | Ala | Glu | Val | Leu | Gly | Val | Leu | Lys | Gln | Ser | Cys | Arg | Gln | Lys |
| | | | | 20 | | | | | 25 | | | | | 30 |
| Ser | Gln | Pro | Ser | Glu | Asp | Val | Ser | Gln | Ala | Asp | Lys | Met | Pro | Ala |
| | | | | 35 | | | | | 40 | | | | | 45 |
| Ser | Glu | Ser | Ser | Thr | Thr | Pro | Leu | Asn | Ile | Leu | Asp | Arg | Val | Ser |
| | | | | 50 | | | | | 55 | | | | | 60 |
| Asn | Lys | Ile | Ile | Ser | Asn | Val | Val | Thr | Phe | Tyr | Asp | Glu | Ile | Asn |
| | | | | 65 | | | | | 70 | | | | | 75 |
| Thr | Asn | Lys | Arg | Pro | Leu | Lys | Ser | Ile | Gly | Arg | Leu | Leu | Asp | Asp |
| | | | | 80 | | | | | 85 | | | | | 90 |
| Asp | Asp | Asp | Glu | His | Asp | Asp | Tyr | Asp | Tyr | Asn | Asp | Asp | Glu | Phe |
| | | | | 95 | | | | | 100 | | | | | 105 |
| Phe | Thr | Asn | Lys | Arg | Gln | Lys | Leu | Ser | Arg | Ala | Ile | Ala | Lys | Gly |
| | | | | 110 | | | | | 115 | | | | | 120 |
| Lys | Asp | Asn | Leu | Lys | Glu | Tyr | Lys | Leu | Asn | Met | Ser | Ile | Glu | Ser |
| | | | | 125 | | | | | 130 | | | | | 135 |

| | | | | | | | | | | | | | |
|---|---|---|---|---|---|---|---|---|---|---|---|---|---|
| Lys | Lys | Arg | Leu | Val 140 | Thr | Cys | Leu | His 145 | Leu | Lys | Leu | Ala | Asn 150 |
| Lys | Gln | Leu | Ser | Asp 155 | Lys | Ile | Ser | Cys | Leu 160 | Gln | Asp | Leu | Val | Glu 165 |
| Lys | Glu | Gln | Val | His 170 | Pro | Leu | His | Lys | Gln 175 | Asp | Gly | Asn | Ala | Arg 180 |
| Thr | Thr | Thr | Gly | Ala 185 | Gly | Glu | Asp | Glu | Thr 190 | Ser | Ser | Asp | Glu | Asp 195 |
| Asp | Asp | Asp | Glu | Glu 200 | Phe | Phe | Asp | Ala | Ser 205 | Glu | Gln | Val | Asn | Ala 210 |
| Ser | Glu | Gln | Ser | Ile 215 | Val | Val | Lys | Met | Glu 220 | Val | Val | Gly | Thr | Val 225 |
| Lys | Lys | Val | Tyr | Ser 230 | Leu | Ile | Ser | Lys | Phe 235 | Thr | Ala | Asn | Ser | Leu 240 |
| Pro | Glu | Pro | Ala | Arg 245 | Ser | Gln | Val | Arg | Glu 250 | Ser | Leu | Leu | Asn | Leu 255 |
| Pro | Thr | Asn | Trp | Phe 260 | Asp | Ser | Val | His | Ser 265 | Thr | Ser | Leu | Pro | His 270 |
| His | Ala | Ser | Phe | His 275 | Tyr | Ala | Asn | Cys | Glu 280 | Glu | Gln | Lys | Val | Gln 285 |
| Gln | Gln | Gln | Gln | Gln 290 | Gln | Gln | Gln | Gln | Gln 295 | Gln | Gln | Gln | Leu | Leu 300 |
| Gln | Gln | Gln | Leu | Leu 305 | Gln | Gln | Gln | Gln | Gln 310 | Lys | Arg | Asn | Lys | Asp 315 |
| Gly | Asp | Asp | Ser | Ala 320 | Ser | Pro | Ser | Ser | Ser 325 | Val | Thr | Ala | Asn | Gly 330 |
| Lys | Val | Leu | Ile | Leu 335 | Ala | Lys | Glu | Ser | Leu 340 | Glu | Met | Val | Arg | Asn 345 |
| Val | Met | Gly | Val | Val 350 | Asp | Ser | Thr | Leu | Gly 355 | Lys | Ala | Glu | Glu | Trp 360 |
| Val | Lys | Gln | Lys | Gln 365 | Glu | Val | Lys | Glu | Met 370 | Ile | Arg | Glu | Arg | Phe 375 |
| Leu | Gln | Gln | Gln | Gln 380 | Gln | Tyr | Arg | Gln | Gln 385 | Gln | Gln | Lys | Asp | Gly 390 |
| Asn | Tyr | Val | Lys | Pro 395 | Ser | Gln | Asp | Asn | Val 400 | Asp | Ser | Lys | Asp | |

INOSITOL-EXCRETING YEAST

This is a continuation of application Ser. No. 07/672,355, filed on Mar. 20, 1991, now abandoned.

FIELD OF THE INVENTION

The present invention is related to the negative regulation of phospholipid biosynthesis in a yeast strain to produce excess inositol. More specifically, the present invention is related to the production of excess inositol from a diploid yeast strain, baker's yeast (*Saccharomyces cerevisiae*), for human or animal consumption.

BACKGROUND OF THE INVENTION

Phospholipid biosynthesis in *Saccharomyces cerevisiae* is regulated in a coordinated fashion. Inositol 1-phosphate synthase [I1PS], Cytidine diphosphate diacylglycerol synthase [CDP-DGS], phosphatidylserine synthase [PSS], phosphatidylserine decarboxylase [PSD] and the phospholipid methyltransferases (PMTs) which convert phosphatidylethanolamine (PE) to phosphatidylcholine (PC), are all subject to regulation by inositol, and choline (See FIG. 1). All of these enzymes show various degrees of repression in cells grown in the presence of inositol, and all display maximal repression when cells are grown in the presence of inositol and choline. However, the enzyme ultimately responsible for the production of PI, phosphatidylinositol synthase (PIS), is not regulated in response to phospholipid precursors.

Several of the phospholipid biosynthetic enzyme activities have been shown to be regulated at the level of transcription of structural genes. The steady-state levels of INO1 mRNA and CHOI mRNA encoding for I1PS and PSS respectively, are reduced when wild type cells are grown in the presence of inositol. The mRNA levels are further reduced when both inositol and choline are present in the growth medium. A similar response has also been observed with the CHO2 and OPI3 genes encoding the PMTs (See FIG. 1).

Several of the coregulated structural genes have also been shown to be controlled by a common set of regulatory genes. Many mutants with defects in the regulation of phospholipid metabolism were originally isolated on the basis of a defect in I1PS regulation. The wild-type products of the regulatory genes INO2 and INO4 are required for expression of INO1. Mutations at either of these two loci result in failure of cells to express I1PS, leading to inositol auxotrophy. The ino2 and ino4 mutants are also unable to derepress the entire set of enzymes that are subject to coordinate control by inositol and choline.

Mutants with lesions at the OPI1 locus were originally isolated by Greenberg, M., Goldwasser, P., and Henry, S. (1982). *Mol. Gen. Genet.* 186, 157–163 and Greenberg, M. L., Reiner, B., and Henry, S. A. (1982). *Genetics 100, 19–33* on the basis of an Over Production of Inositol Phenotype (Opi⁻). The opi1 mutants constitutively express derepressed levels of I1PS, as well as many of the other coregulated enzymes. The effect of the opi1 regulatory mutation is also apparent at the level of mRNA. In opi1 mutants, INO1 transcript is constitutively overexpressed regardless of the growth condition. Thus, the opi1 gene, SEQ ID NO: 1, is believed to encode a negative regulatory factor that is required to repress the whole subset of enzymes that are coordinately controlled by inositol and choline.

Results from a deletion analysis of the 5' untranslated region of INO1 show there are cis-acting regulatory sites that act to reduce transcription of this gene under repressing growth conditions. See Hirsch, J. P., Lopes, J. M., Chorgo, P. A., and Henry, S. A. (1991). *Nucl. Acids Res.* Submitted. In order to understand the mechanism by which the OPI1 gene, SEQ ID NO: 1, and its product, SEQ ID NO: 2, interact with other regulatory genes and the structural genes under their control, a detailed molecular analysis of the OPI1 gene, SEQ ID NO: 1, has been achieved. The present invention presents the genetic mapping, cloning and molecular analysis of the OPI1 gene, SEQ ID NO: 1, and the use of it and its gene product, SEQ ID NO: 2, in phospholipid biosynthesis to excrete excess inositol, for instance, for human or animal consumption.

SUMMARY OF THE INVENTION

The present invention pertains to a yeast cell, preferably *Saccharomyces cerevisiae*, which contains a functional stable recombinant DNA sequence that does not allow for the encoding of a negative regulator of phospholipid biosynthesis therein.

In a preferred embodiment, the recombinant DNA sequence is an OPI1 gene deletion which results in the deregulation of inositol or inositol-containing metabolites such as inositol-1-phosphate synthase.

The present invention pertains to a method for obtaining inositol, inositol-containing metabolites or phospholipids such as myo-inositol or inositol-1-phosphate. The method comprises the steps of genetically engineering a stable yeast cell, preferably *Saccharomyces cerevisiae*, to continually produce inositol, inositol-containing metabolites or phospholipids. Additionally, there is the step of then generating the inositol, inositol-containing metabolites or phospholipids.

In a preferred embodiment, the genetically engineering step includes the step of altering the negative regulatory step involved in phospholipid biosynthesis to overproduce inositol, inositol-containing metabolites or phospholipids such as myo-inositol.

BRIEF DESCRIPTION OF THE DRAWINGS

In the accompanying drawings, the preferred embodiments of the invention and preferred methods of practicing the invention are illustrated in which:

FIGS. 8a through 8f illustrate the nucleotide sequence, SEQ ID NO: 1, and predicted amino acid sequence, SEQ ID NO: 2, of the OPI1 gene. The leucine residues of the leucine zipper are underlined and polyglutamine stretches are located within extended boxes. Positions of nonsense codons in isolated opi1 mutant allels are marked with an asterisk.

DESCRIPTION OF THE PREFERRED EMBODIMENT

Figure 1:
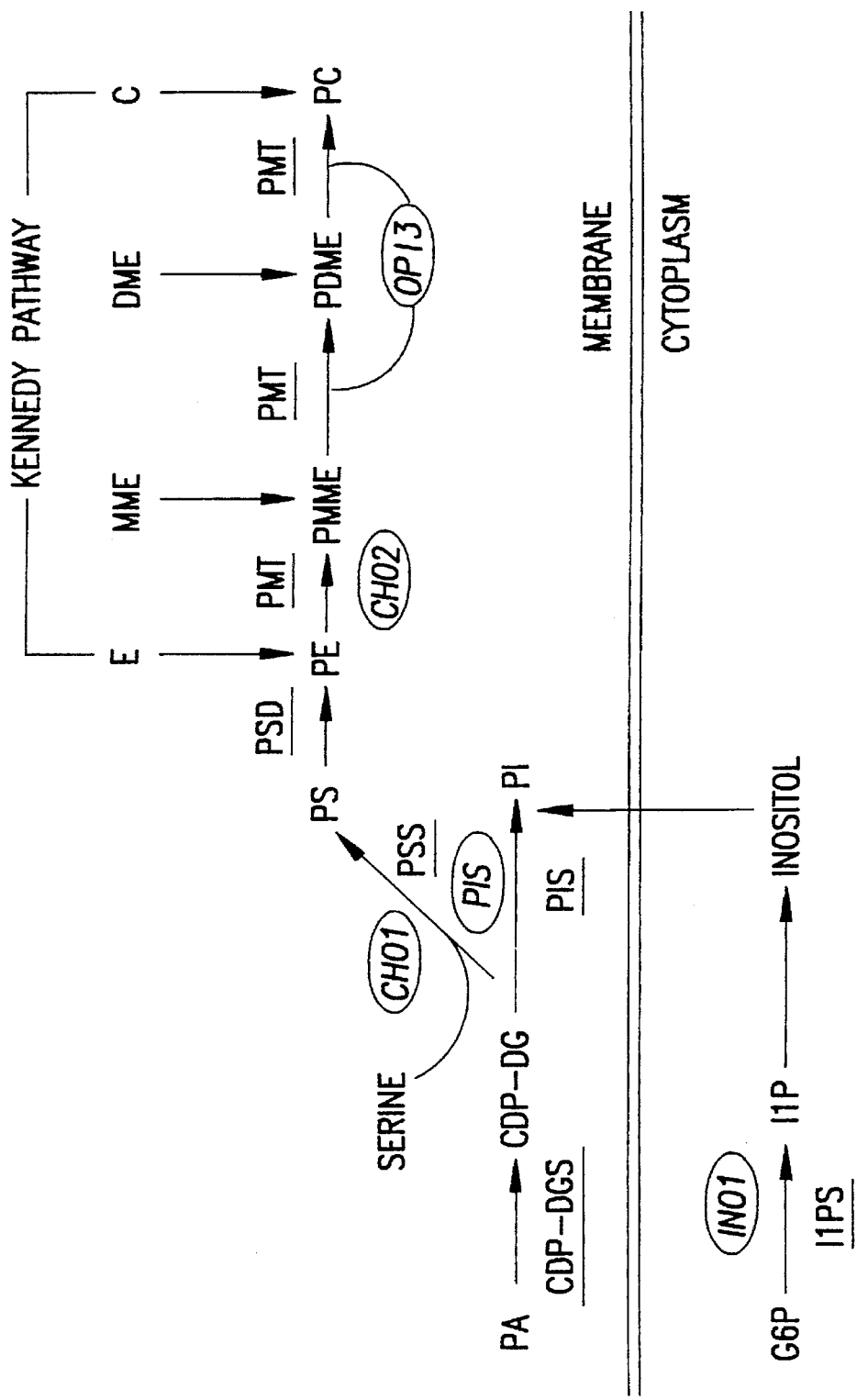
FIG. 1 illustrates pathways for phospholipid biosynthesis in *Saccharomyces cerevisiae*.

The present invention pertains to a yeast cell, such as brewer's yeast or baker's yeast (*Saccharomyces cerevisiae*). The yeast cell contains a functional stable recombinant DNA sequence that does not allow for the encoding of a negative regulator of phospholipid biosynthesis therein. The recombinant DNA sequence preferably does not allow for the encoding of a negative regulator of inositol or inositol-containing metabolites.

Preferably, the recombinant DNA sequence is an OPI1 gene deletion. The OPI1 gene, SEQ ID NO: 1, encodes the negative regulator Opi1p. Preferably, the OPI1 gene has a nucleotide (SEQ ID NO: 1) and amino acid (SEQ ID NO: 2) sequence as shown in FIG. 8. The Opi1p consists of 404 amino acid residues that has a molecular weight of 40,036. The Opi1p contains polyglutamine tracks and a leucine zipper.

The present invention also pertains to a method for obtaining inositol, inositol-containing metabolites or phospholipids. The method comprises the steps of first genetically engineering a stable yeast cell to continually produce inositol, inositol-containing metabolites or phospholipids and then generating the inositol, inositol-containing metabolites or phospholipids. The yeast cell can be brewer's yeast or preferably baker's yeast, *Saccharomyces cerevisiae* as described herein.

In an alternative embodiment, the yeast cell has multiple copies of an INO1 gene. There can be, for instance, three to six copies of the INO1 gene therein.

A method of producing the yeast cells having multiple copies of the INO1 gene comprise the steps of first creating a plurality of plasmids each of which have at least one copy of an INO1 gene. Then, inserting the plurality of plasmids into the yeast cells such that the yeast cells have multiple copies of the INO1 gene in a stable configuration. Preferably, before the inserting step, there is the step of eliminating the ability of the cells to encode a negative regulator of a phopholipid biosynthesis.

Additionally, each plasmid preferably also has a URA3 marker; and including before the eliminating step, the step of cutting the plasmids internal to the URA3 marker such that the plasmid is linearized. Moreover, the cells have an URA3 locus and wherein the inserting step includes the step of inserting linearized plasmids into the cells such that they are directed to the URA3 locus of the cells. Preferably, the cells are haploid yeast cells and after the inserting step, there is the steps of identifying the haploid cells having multiple copies of the INO1 gene and the step of mating the haploid cells to form diploid cells.

A computer disc having the INO1 and the OPI1 (SEQ ID NO: 1) data sequences in computer readable form is included in Appendix A herein. The computer disc with the DNA sequence was produced from a Macintosh™ PC with the computer program titled Spider. Additionally, these DNA sequnces are present in the GenBank™/EMBL database. The OPI1 DNA sequence, SEQ ID NO: 1, can be accessed therethrough with access number M57383, and the INO1 DNA sequence can be accessed therethrough with access number J04453. The *Saccharomyces cerevisiae* of the single copy and the INO1 multicopy embodiment were deposited in the American Type Culture Collection depository on Feb. 13, 1991 under ATCC designation numbers 74033 and 74034, respectively.

The following discloses the preferred materials and methods by which the OPI1 gene (SEQ ID NO: 1) is mapped, cloned and molecularly analyzed, leading to the construction of a diploid opi1 deletion mutant containing either two copies of the INO1 structural gene or multiple insertions of the INO1 gene. For routine bacterial transformations and maintenance of plasmids, *Escherichia coli* DH5 α [F⁻, endA1,hsdR17($r_k$⁻, $m_k$⁺),supE44,thi-1, recA1, gyrA 96, relA1, Δ(argF-lac zya) U169, φ80d lacZ Δ M15, λ⁻] (Hanahan, D., 1983). *J. Mol. Biol.* 166, 557–580 was used. While *E. coli* XL1-Blue [recA1,endA1,gyrA96,thi,hsdR17($r_k$⁻, $m_k$+),supE44,relA1 λ⁻,lac⁻, {F',proAB,lacI$^Q$,lacZ Δ 15, Tn10(tet$^R$)}] (Bullock, W. O., Fernandez, J. M., and Short, J. M. 1987). *Biotechniques* 5, 376–379 is used for single stranded DNA (ssDNA) production.

The genotypes and sources of *Saccharomyces cerevisiae* strains used with respect to the OPI1 are presented in Table 1.

The following growth media and genetic methods are also used; *Escherichia coli* DH5 α cells used to propagate plasmid DNA were grown in LB medium containing 50 μgml⁻¹ ampicillin. Bacterial strain XL1-Blue used for the production of ssDNA is a lac⁻AG1 derivative with Tn10, lacI$^Q$ and lac Δ M15 on the F'. Selection for organisms containing F' is accomplished by addition of 10 μgml⁻¹ tetracycline to the above medium. Plates that have been spread with 50 μl 100 mM IPTG and 50 μl 2% (w/v) X-gal in dimethylformamide are used to detect colonies with plasmids containing yeast genomic-DNA inserts. All bacterial strains are incubated at 37° C.

Media used for growth and sporulation of yeast have been described by Sherman, F., Fink, G. R., and Lawrence, C. W. (1978). *In Methods Yeast Genetics*, Cold Spring Harbor Laboratory, N.Y. For routine culture, YEPD medium (1% yeast extract, 2% peptone, 2% glucose) is used. The synthetic complete medium contained in (L⁻¹): glucose, 20 g; vitamin-free yeast nitrogen base (Difco), 6.7 g; biotin, 2 μg; calcium pantothenate, 400 μg; folic acid, 2 μg; niacin, 400 μg; p-aminobenzoic acid; 200 μg; pyridoxine hydrochloride, 400 μg; myo-inositol, 2 mg; lysine, 20 mg; arginine, 20 mg; methionine, 20 mg; threonine, 300 mg; tryptophan, 20 mg; leucine, 60 mg; histidine, 10 mg; adenine, 20 mg; uracil, 40 mg; and agar (for plates only), 20 g. Auxotrophic markers are checked on medium lacking a single component of the complete medium (drop-out medium). Inositol-free medium (I⁻) is identical to synthetic complete medium with the exception that myo-inositol has been omitted. As described by Ruby, S. W., Szostak, J. W., and Murray, A. W. (1983). *Methods Enzymol.* 101, 253–267, a buffered medium used to score β-galactosidase activity consists of all components of synthetic complete medium except vitamin-free yeast nitrogen base, with the addition of 0.1M $KH_2PO_4$ (pH7.0), 15 mM $[NH_4]_2SO_4$, 0.8 mM $MgSO_4.7H_2O$, 2 μM $FeSO_4.6H_2O$, 75 mM KOH, and 0.04 mgml⁻¹ X-gal. Where indicated media is supplemented with 10 μM or 75 μM myo-inositol and/or 1 mM choline chloride. In all work involving *S. cerevisiae*, cultures are incubated at 30° C.

Bacterial strains were transformed with plasmid DNA following the calcium chloride procedure described by Mandel, M., and Higa, A. (1970). *J. Mol. Biol.* 53, 159–162. Yeast strains are transformed with isolated plasmid DNA using the lithium acetate method described by Ito, H., Yasuki, F., Murata, K., and Kimura, A. (1983). *J. Bacteriol.* 153, 163–168 and modified by Hirsch, J. P., and Henry, S. A. (1986). *Mol. Cell. Biol.* 6, 3320–3328. Where indicated, directed transformations and gapped-plasmid transformations are performed by digesting plasmids at specific endonuclease restriction sites.

The following methods are used to assay for Opi⁻ [Over Production of Inositol] phenotype:

1. Strains of *S. cerevisiae* are tested for the Opi⁻ phenotype by a modification of the method first described by Greenberg, M., Goldwasser, P., and Henry, S. (1982). *Mol. Gen. Genet.* 186, 157–163 and Greenberg, M. L., Reiner, B., and Henry, S .A. (1982). *Genetics* 100, 19–33.

Figure 2:
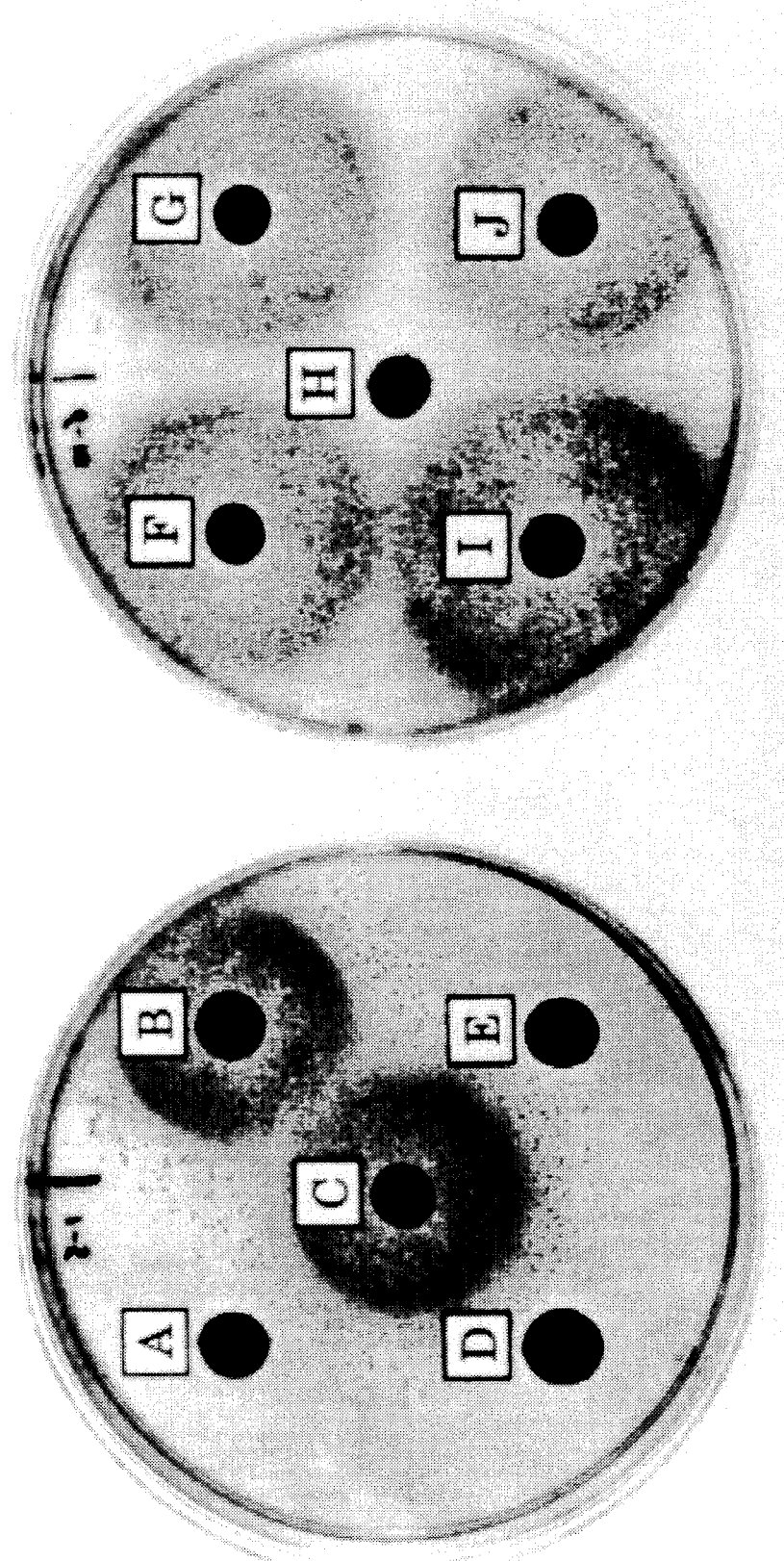
FIG. 2 illustrates a bioassay for the Opi⁻ phenotype. Overproduction and excretion of inositol by strains results in the growth of the indicator strain around the patch of cells.

2. Strains are patched into I⁻ plates and, after 24h incubation, sprayed with a suspension of a tester strain (AID) in sterile distilled water. The tester strain is a diploid homozygous for an ade1 marker, which confers a red phenotype and an INO1 marker, which confers inositol auxotrophy (Table 1). Overproduction and excretion of inositol by strains results in growth of the tester strain as seen by a red halo around the patch (See FIG. 2).

TABLE 1

List of *S. cerevisiae* strains used in this study

| Strain designation | Genotype |
| --- | --- |
| AID | ade1/ade1 ino1/ino1 MATa/α |
| DC5 | his3–11,15 leu2–3, –112 MATa |
| W303-1A | ade2–1 can1-100 his 3–11, –15 leu2–3, –112 trp1–1 ura3–1 MATa |
| WT1 | leu2–3, –112 MATα |
| WT2 | ade5 leu2–3, –112 MATα |
| jH0-6D | opi1–1 ade5 leu2–3, –112 trp1–1 ura3–1 MATa |
| JH2-3D | opi1–1 hom3 MATa |
| JH2-7C | spo11 ade2 MATα |
| NO80 | opi1–2 his3–11, –15 leu2–3, –112 MATa |
| NO99 | opi1–3 his3–11, –15 leu2–3, –112 MATa |
| OP1 | opi1–1 lys2 MATα |
| OP12 | opi1–12 lys2 MATα |
| OP-lacZ | opi1–1 ade5 leu2–3, –112 trp1–1 URA3 (pJH334, INO1'lacZ) ura3–1 MATa |
| OP-Δ1 | opi1–::LEU2 leu2–3, –112 his3–11, –15 MATa |
| OP-Δ2 | opi1–Δ::LEU2 leu2–3, –112 his3–11, –15 MATa |
| DD1 | opi1–::LEU2/OPI1 his3–11, –15/ |

TABLE 1-continued

List of *S. cerevisiae* strains used in this study

| Strain designation | Genotype |
| --- | --- |
| | HIS3 leu2–3, –112/leu2–3, –112 MATa/α |
| DD2 | opi1–::LEU2/opi1–1 his3–11, –15/ HIS3 leu2–3, –112/LEU2 LYS2/ lys2 MATa/α |
| DD3 | opi1–::LEU2/opi1–12 his3–11, –15/ HIS3 leu2–3, –112/LEU2 LYS2/ lys2 MATa/α |

3. Strains transformed with genomic DNA in high-copy shuttle vectors or centromeric are assayed using I⁻ plates lacking leucine or uracil.

The chromosomal mapping, cloning and subcloning of the OPI1 gene (SEQ ID NO: 1) are done as follows:

1. The SPO11-maping technique described by Klapholtz, S., and Esposito, R. E. (1982). *Genetics* 100, 387–412 was chosen to map the OPI1 locus.

a. This procedure utilizes the ability of diploid strains homozygous for the spo11-1 mutation to undergo chromosomal segregation without appreciable recombination during sporulation.

b. While constructing strains required for the SPO11-mapping technique, it was determined that the OPI1 gene (SEQ ID NO: 1) and SPO11 gene are on the same chromosome and not separable by recombination.

2. A 9.5 kilobase (kb) yeast genomic clone containing the SPO11 gene, p(SPO11)1, was obtained from C. Atcheson and R. Esposito and used to transform an opi1 mutant strain (JH0-6D).

a. This 9.5 kb fragment has been cloned into the yeast centromeric plasmid YCp19, Stinchcomb, D. T., Mann, C., and Davis, R. W. (1982). *J. Mol. Biol.* 158, 157–179; (Table 2).

b. Two additional clones were obtained from C. Atcheson and R. Esposito that had been used to localize the SPO11 gene and were tested for their ability to complement an opi1 mutation (See FIG. 3).

c. Plasmid p(SPO11]3 is a 4.0 kb BamH1-HindIII fragment from p(SPO11)1 cloned into YCp50, Johnston, M., and Davis, R. W. (1984). *Mol. Cell. Biol.* 4, 1440–1448 and p(SPO11)9 is a SalI digest of p(SPO11)1religated (Table 2).

TABLE 2

List of plasmid constructions

| Plasmid | Subclone | Vector |
| --- | --- | --- |
| p(SPO11)1 | 9.5 kb from yeast genomic DNA | YCp19 |
| p(SPO11)3 | 4.0 kb BamHI-HindIII from p(SPO11)1 | YCp50 |
| p(SPO11)9 | SalI digest/religation of p(SPO11)1 | YCp19 |
| pJH334 | 1.0 kb BglII-PstI 5'INO1 DNA in frame with lacZ | YIp357R |
| pJH344 | 2.8 kb BamHI–SalI from p(SPO11)3 | YEp351 |
| pJH354 | 2.8 kb SstI–HindIII from p(SPO11)3 | YEp351 |
| pJH355 | 1.2 kb BglII–HindIII from p(SPO11)3 | YEp351 |

TABLE 2-continued

List of plasmid constructions

| Plasmid | Subclone | Vector |
|---------|----------|--------|
| pMW10 | 2.0 kb XhoI—XhoI from pJH354 | YEp352 |
| pMW11 | 2.0 kb XhoI—XhoI from pJH354 (opposite orientation) | YEp352 |
| pMW12 | 1.3 kb EcoRV–HindIII from pJH354 | YEp352 |
| pMW13 | 0.8 kb EcoRV–HindIII from pJH354 | YEp352 |
| pMW14 | 2.0 kb SstI–PstI from pMW10 | YIp351 |
| pMW15 | 2.0 kb SstI–PstI from pMW11 | YIp351 |
| pMW16 | 3.0 kb BglII—BglII LEU2 into pMW10 | YEp351 |
| pMW17 | 3.0 kb BglII—BglII LEU2 into pMW10 (opposite orientation) | YEp352 |
| pMW18 | 3.0 kb BglII—BglII LEU2 into pMW11 | YEp352 |
| pMW19 | 3.0 kb BglII—BglII LEU2 into pMW11 (opposite orientation) | YEp352 |
| pMW20 | 2.2 kb SalI–XhoI LEU2 into XhoI—XhoI Δ of pJH354 | YEp351 |
| pMW21 | 2.2 kb SalI–XhoI LEU2 into XhoI—XhoI Δ of pJH354 (opposite orientation) | YEp351 |
| pMW22 | 1.5 kb SpeI–XhoI from pMW10 | YEp352 |
| pMW23 | 1.4 kb NaeI–XhoI from pMW10 | YEp352 |
| pMW24 | 1.0 kb DraI–XhoI from pMW10 | YEp352 |

3. The yeast/*E. coli* shuttle vectors described by Hill, J. E., Myers, A. M., Koerner, T. J., and Tzagoloff, A. (1986). *Yeast* 2, 163–167 are used to construct additional subclones (Table 2).

a. The BamHI-SalI, SstI, HindIII and BglII-HindIII fragments from p(SPO11)3 are cloned into YEp351 to give pJH344, pJH354 and pJH355 respectively.

b. Fragment XhoI-XhoI from pJH354 is cloned in both orientations, into the SalI site of YEp352 to give plasmids pMW10 and pMW11.

c. The fragments EcoRV-HindIII and EcoRV-XhoI from pJH354 are cloned into the SmaI-HindIII and SmaI-SalI sites of YEp352 to give plasmids pMW12 and pMW13 respectively.

d. Cloned fragments of pMW10 and pMW11 are also cloned into YIp351, using the SstI-PstI sites of YEp352, to give plasmids pMW14 and pMW15 respectively (Table 2). All of these subclones are tested for their ability to complement the opi1 mutant phenotype (See FIG. 3).

Yeast strains carrying an INO1'lacZ fusion are constructed as follows. Mutations in the OPI1 gene result in constitutive expression of the INO1 gene. In order to obtain a plate phenotype based on the β-galactosidase assay, strains carrying a section of the INO1 promoter fused to the lacZ reporter gene of *E. coli* are constructed. The integrating plasmid pJH334, [Hirsch, J. P., Lopes, J. M., Chorgo, P. A., and Henry, S. A. (1991). *Nucl. Acids Res. Submitted*; (See Table 2)] is used to transform yeast strains. This plasmid has been constructed from the lacZ-fusion vector YIp357R [Myers, A. M., Tzagoloff, A., Kinney, D. M., and Lusty, C. J. (1986). *Gene* 45, 299–310] and contains a 1.0 kb fragment of 5' INO1 DNA fused in frame with lacZ. In previous studies, this fusion was shown to be fully regulated in response to inositol and choline and be expressed constitutively in an opi1 mutant background, Hirsch, J. P., Lopes, J. M., Chorgo, P. A., and Henry, S. A. (1991). *Nucl. Acids Res. Submitted*. Plasmid DNA that had been linearized at the URA3 selectable marker with StuI is used to transform Ura⁻ strains W303-1A and JH0-6D.

The opi1-1 strain OP-lacZ (Table I) carrying a single copy of the INO1'lacZ fusion, is also transformed with plasmid pMW14 or pMW15. Each of these are directed to the OPI1 locus by linearizing the plasmid at the BglII site. All transformants are tested for β-galactosidase activity using X-gal plates with and without phospholipid precursors, inositol and choline.

Figure 7:
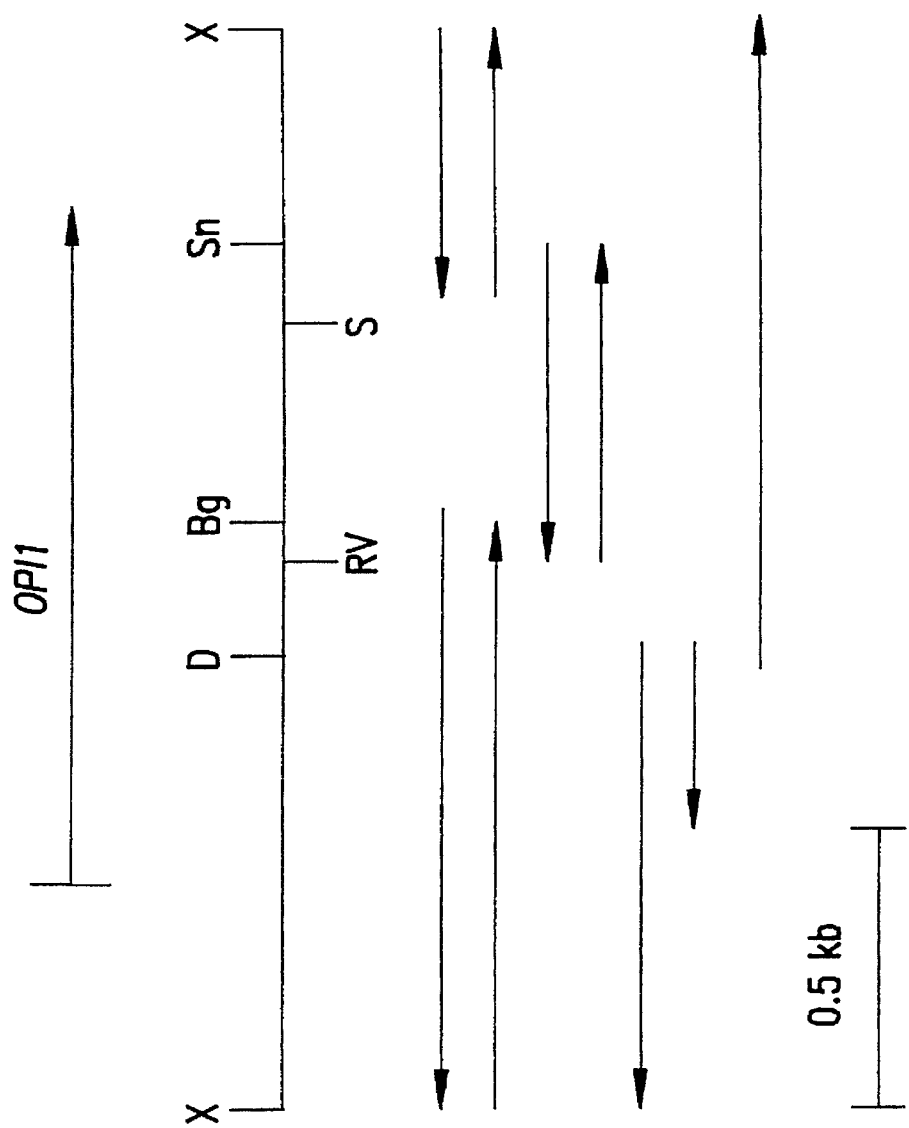
FIG. 7 illustrates the sequency strategy. The arrows indicate the direction of ssDNA sequencing and the arrow labelled OPI1 indicate the position of the OPI1 coding region (SEQ ID NO: 1) and direction of transcription.

The isolation of DNA and RNA is described below. Plasmid DNA is isolated from transformed bacterial strains either by the boiling miniprep method, originally described by Holmes, D. S., and Quigley, M. (1981). *Anal. Biochem.* 114, 193–197, or the CsCl-EtBr gradient procedure used by Clewell, D. B., and Helinski, D. R. (1969). *Proc. Natl. Acad. Sci. USA* 62, 1159–1166. Plasmids used for the preparation of sequencing templates are constructed by inserting agarose-gel purified OPI1 restriction fragments, from plasmids pMW10 and pMW11, into the vector pGEM™-5Zf(+) [Promega Biotech; See FIG. 7]. For induction of ssDNA, *E. coli* XL1-Blue cells containing pGEM-5Zf(+) recombinants are infected with the helper phage M13K07 (Promega Biotech). Single-stranded DNA exported from bacterial cells as encapsidated virus-like particles is purified by simple precipitation and extraction procedures. Isolation of yeast-genomic DNA for Southern-blot analysis is performed using the method described by Hoffman, C. S., and Winston, F. (1987). *Gene* 57, 267–272. Total yeast RNA from organisms grown in the presence and absence of phospholipid precursors is isolated using the glass-bead disruption and hot-phenol extraction procedure of Elion, R. A., and Warner, J. R. (1984). *Cell* 39, 663–673.

The following methods are used to construct the OPI1 disruption alleles:

1. Plasmids containing disrupted OPI1 fragments are constructed using either pMW10/pMW11 or pJH354 (Table 2).

2. Plasmid pMW10 or pMW11 is linearized at the BglII site, which is internal to the cloned DNA, and a 3.0 kb BglII-BglII LEU2 gene-fragment from YEp13 is inserted in either orientation. This gives rise to plasmids pMW16, pMW17, pMW18 and pMW19 (Table 2).

Figure 4A:
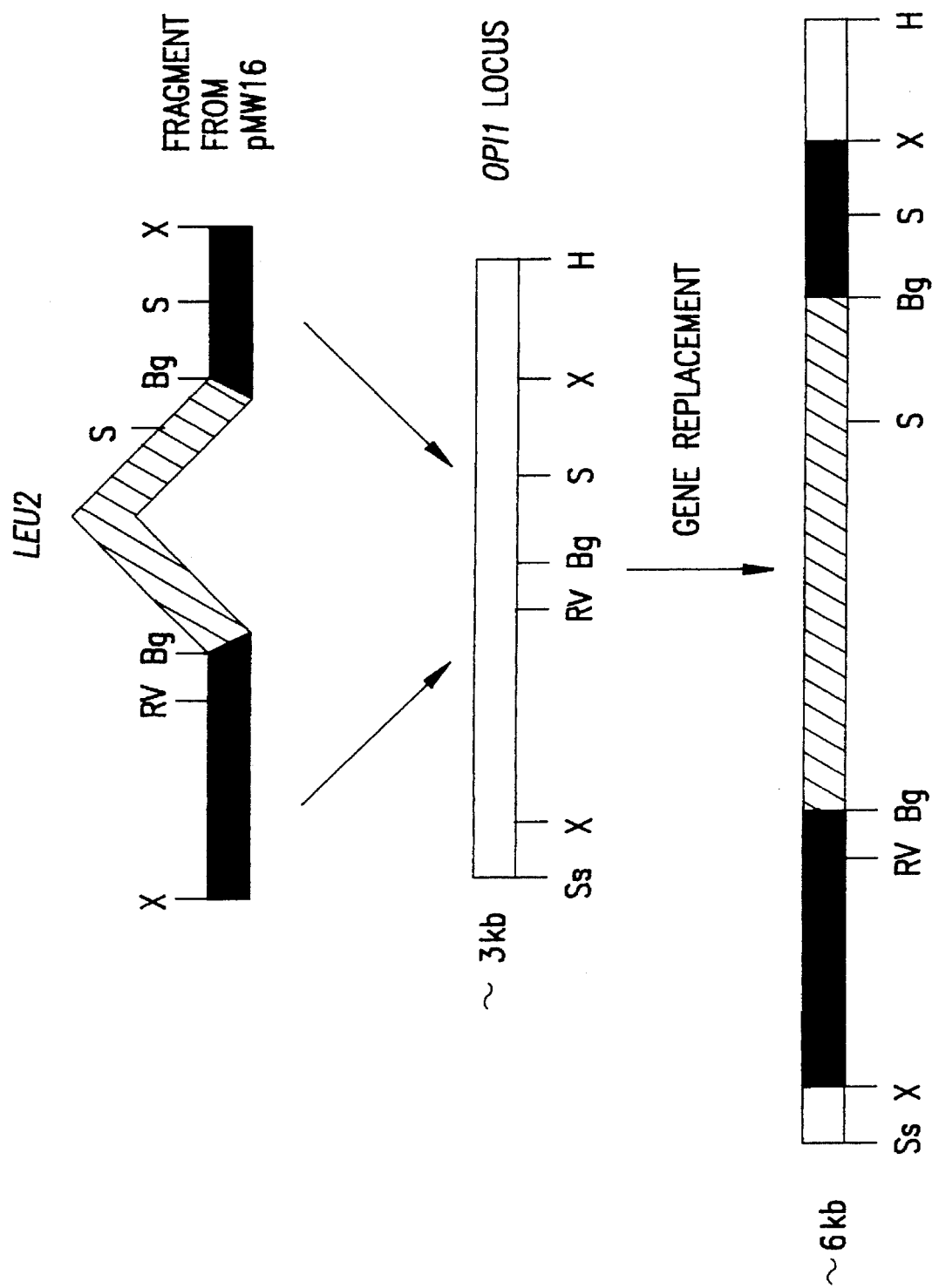
FIG. 4a illustrates an insertion whereby a LEU2 selectable marker was inserted into the OPI1 coding region (SEQ ID NO: 1).
Figure 4B:
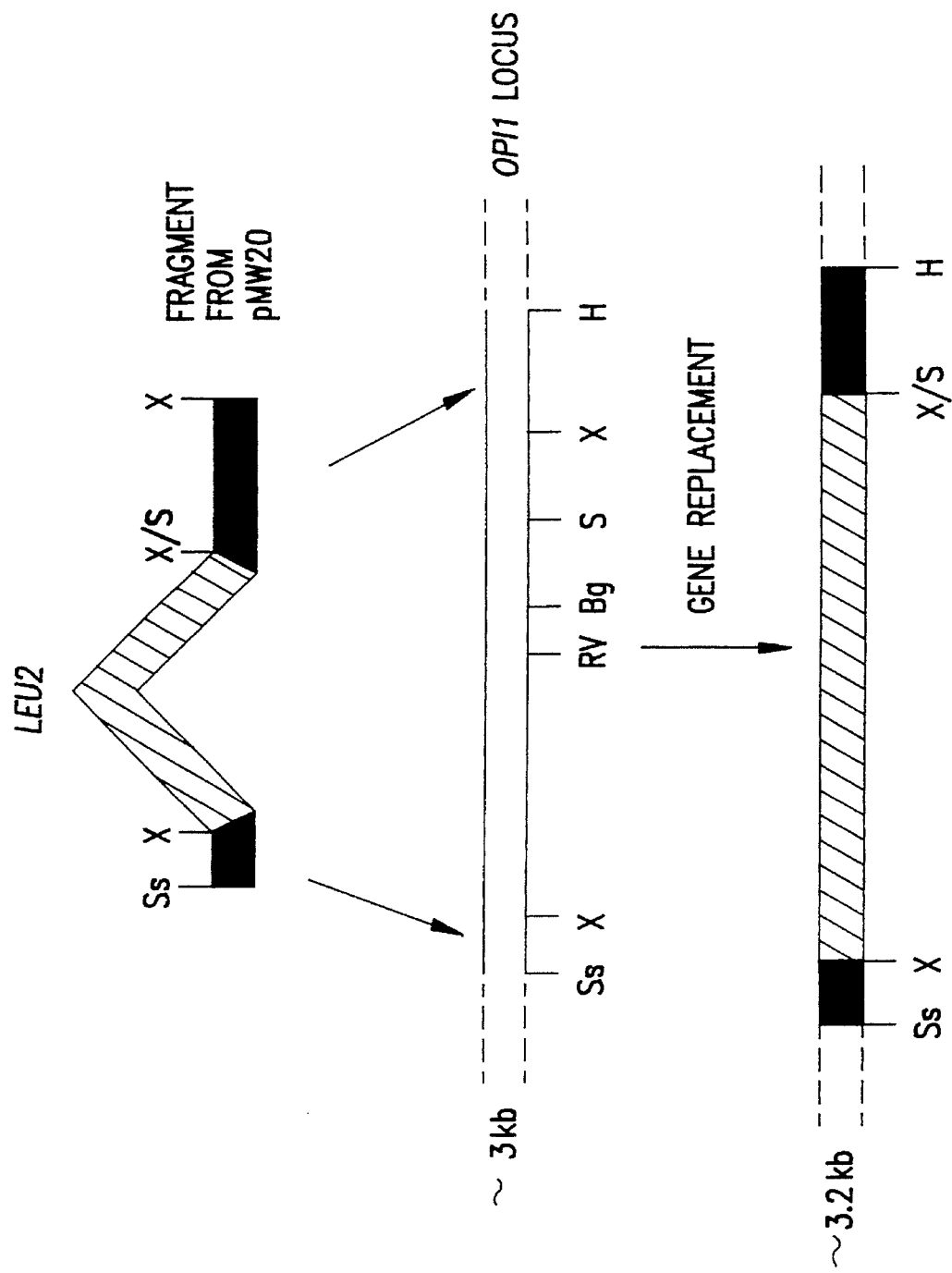
FIG. 4b illustrates a deletion whereby the whole OPI1 coding region (SEQ ID NO: 1) was removed and replaced with a LEU2 selectable marker.

3. Plasmid pJH354 is digested with the restriction endonuclease XhoI, so as to remove a 2.0 kb fragment from the cloned OPI1 gene fragment, and a 2.2 kb SalI-XhoI LEU2 gene-fragment from YEp13 is inserted in either orientation, giving plasmids pMW20 and pMW21 [Table 2]. The OPI1 gene-fragments containing the selectable LEU2 yeast gene is liberated from plasmids by cutting with SstI-HindIII (See FIGS. 4a and 4b) and used in a one-step disruption transformation of a haploid strain (DC5) wild-type for OPI1 as described by Rothstein, R. J. (1983). *Methods Enzymol.* 101, 202–211.

The following methods are used to construct diploid opi disruption strains containing multiple insertions of the gene, INO1, encoding for inositol-1-phosphate synthesis.

Southern-blot analysis as taught by Southern, E. M. (1975). *J. Mol. Biol.* 98, 503–517 is done as follows. Yeast genomic DNA is digested for 6–7 hours with the appropriate restriction enzymes and analyzed by blot hybridization. Digested DNA is subjected to electrophoresis through a 1% (w/v) agarose gel in 89 mM Tris base-89 mM boric acid-2mM EDTA (pH8.0) (TBE) and transferred to nitrocellulose (0.45 μM poresize; S & S NC, Schleicher and Schuell, Inc.) as described by Maniatis, T., Fritsch, E. F. and Sambrook, J.

(1982) in *Molecular Cloning, A Laboratory Manual*, Cold Spring Harbor Laboratory, N.Y. Blots were prehybridized and $^{32}$P-labelled nick-translated probes hybridized at 37° C. according to the procedure of Maniatis, et al. (1982).

Northern and slot-blot analysis are done as described below:

1. Total yeast RNA is fractionated on a 1.2% [W/V] agarose-3% (V/V) formaldehyde-20 mM 3-(N-morpholino)-propanesulfonic acid [pH7.4]-1 mM EDTA gel and transferred to nitocellulose as described by Thomas, P. S. (1980). *Proc. Natl. Acad. Sci USA* 77, 5201–5205.

2. Slot blots of total yeast RNA are prepared using a Hybrilot slot-blot manifold [Bethesda Research Laboratories].

3. Total RNA [1,2 and 3 µg] is applied directly to nitrocellulose under high-salt conditions [3MNacl, 0.3M $Na_3C_6H_5O_7.2H_2O$]

4. Northern blots and slot blots are prehybridized and $^{32}$P-labelled ssRNA probes, synthesized using SP6 polymerase (Boehringer Mannheim Biochemicals), hybridized as described for Southern blots with the exception that the incubation temperature was 53° C.

5. Slot-blot hybridization signals are quantitated after a visual examination using Kodak X-Omat AR X-ray film [Eastman Kodak Company], by cutting out each slot and counting its radioactivity using a Beckman LS5801 liquid scintillation counter (Beckman Instruments, Inc.).

Single-stranded DNA templates are sequenced using the dideoxy chain-termination procedure first described by Sanger, F., Nicklen, S., and Coulsen, A. R. (1977). *Proc. Natl. Acad. Sci. USA* 74, 5463–5467. The universal M13 primer is annealed to ssDNA templates and DNA sequencing performed using a Sequenase kit [United States Biochemical Corp.]. The radionucleotide [$\alpha$-$^{35}$S] ATP (Amersham) is used in all labelling reactions. Routinely, 4–8% (W/V) polyacrylamide-7M urea wedge-gels (0.2–0.8 mm) are used and run on an IBI Standard Sequencer [Model STS 45; International Biotechnologies, Inc.) at a constant 80 watts. Sequencing gels are not fixed before exposure to X-ray film, but dried directly onto Whatman 3M filter paper as described by Kraft, R., Tardiff, J. Krauter, K. S. and Leinwand, L. A. (1988). *Biotechniques* 6, 544–547.

The DNA Strider program (version 1.0) and PC/Gene (version 6.01) are used for immediate analysis of the OPI1 nucleotide and protein sequences. Both GenBank (version 60.0) and EMBL (version 18.0) libraries on BIONET were searched to find nucleotide sequences similar to that of OPI1 (SEQ ID NO: 1). Protein databases NBRF-PIR (version 20.0) and SWISS-Prot (version 10.0) on BIONET were searched for protein sequences similar to the predicted polypeptide sequence of OPI1.

Plasmid-borne copies of several opi1 mutant alleles are obtained using the gap-repair procedure described by Orr-Weaver, T. L., Szostak, J. W., and Rothstein, R. J. (1983). *Methods Enzymol.* 101, 228–245. This technique utilizes the ability of yeast to repair gaps in cloned genes using information from chromosomal DNA. Thus, when a gapped plasmid is used to transform a strain harboring a mutant allele, and the deletion extends past the chromosomal mutation, the mutated sequence is copied onto the plasmid. Using the integrating plasmid pMW14 (Table 2), a series of four gapped plasmids are constructed that had sequences deleted from the OPI1 coding region. These are a 141bp SpeI-NaeI deletion, a 602 bp NaeI-BglII deletion, a 315bp BglII-SalI deletion and a 194bp SalI-NsiI deletion. Three opi1 mutant strains, JHO-6D, NO80 and NO99, are transformed with each of the four gapped-plasmids and all Leu$^+$ transformats assayed for the Opi$^-$ phenotype. Transformants that retained the Opi$^-$ phenotype are assumed to have an integrated copy of the repaired gapped-plasmid, resulting in two copies of the gene each containing the mutant allele. Genomic DNA was isolated from several Leu$^+$Opi$^-$transformants, as previously described. By digesting 5–10 µg. of DNA with any restriction endonuclease that cut once within the cloned DNA and ligating under dilute conditions, plasmids containing the mutant alleles are re-isolated. Plasmids containing mutant allels are amplified using the *E. coli* strain DH5 α and the repaired gaps are subcloned into sections for ssDNA sequencing, as previously described.

The chromosomal mapping, cloning and localization of the OPI1 gene, SEQ ID NO: 1, is obtained as follows. The OPI1 gene is assigned to a chromosomal map position to determine its location with respect to other genes involved in phospholipid biosynthesis. Crosses to strains bearing the spo11 mutation, Klapholtz, S., and Esposito, R. E. (1982). *Genetics* 100, 387–412, indicated that the OPI1 gene is tightly linked to SPO11 on chromosome VIII. When a haploid strain carrying an opi1-1 allele (JH2-3D) is crossed to a haploid strain containing a spo11-1 allele (JH2-7C) and the diploids sporulated, of 46 tetrads examined, 43 contain spores with the parental configuration (i.e., opi1, SPO11 or OPI1 spo11). In these tetrads, the opi1 and SPO11 alleles segregate $2^+:2^-$. The other three tetrads have a 3:1 segregation pattern for the opi1 mutation and are most likely a result of a gene conversion event at the OPI1 locus. Thus, OPI1 and SPO11 are on the same chromosome and recombine with a frequency of less than 2%.

Figure 3:
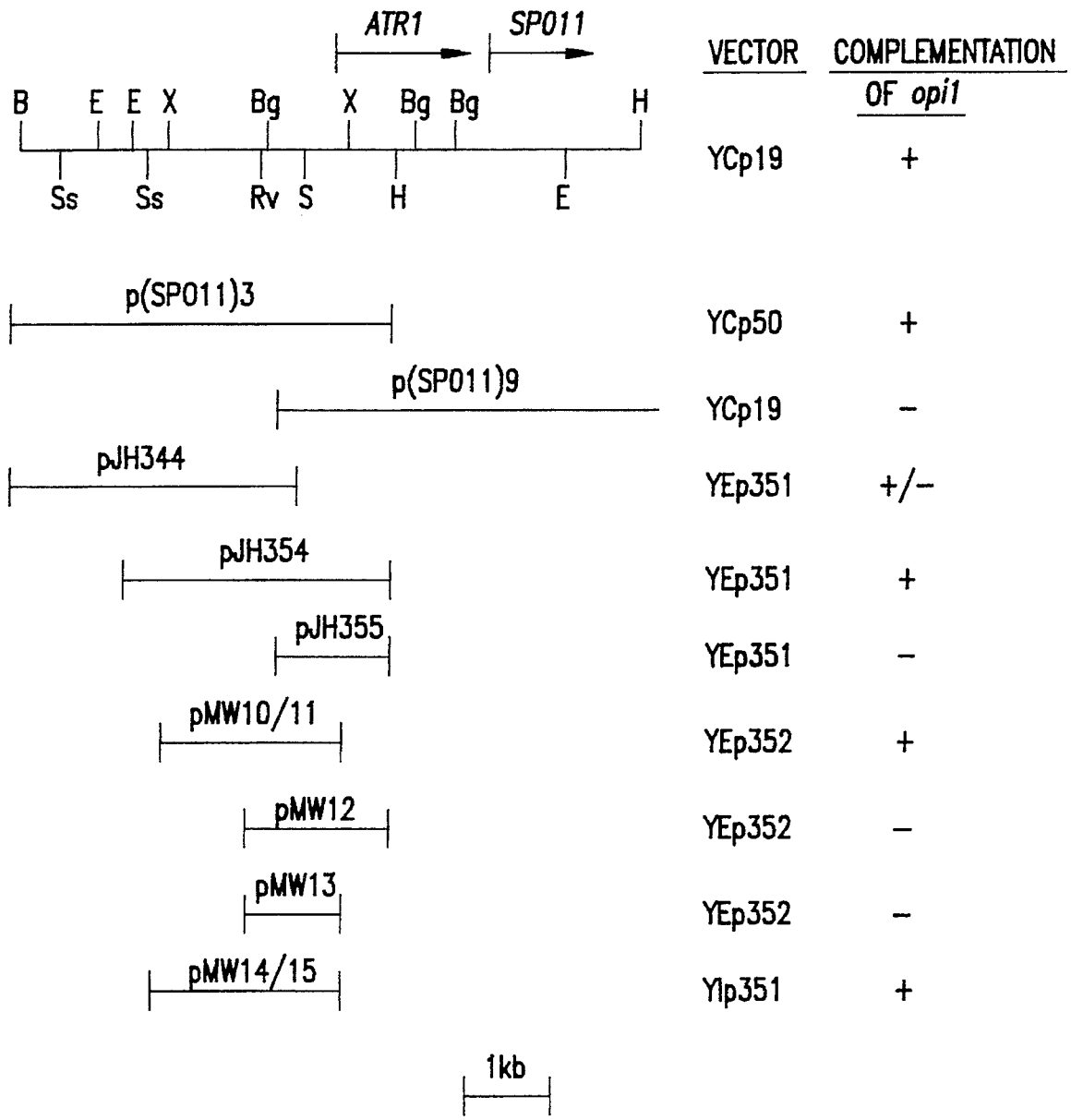
FIG. 3 illustrates restriction mapping, subcloning and complementation of the Opi⁻ phenotype. Ability of subclones to complement opi1 mutant strains is indicated with a (+), inability to complement is indicated with a (−) and partial complementation is indicated with a (±).

Three clones, p(SPO11)1, p(SPO11)3, and p(SPO11)9 that are used to localize the SPO11 gene were generously provided by C. Atcheson and R. Esposito. See Atcheson, C. L., DiDomenico, B., Frankman, S., Esposito, R. E. and Elder, R. T. (1987). *Proc. Natl. Acad. Sci. USA* 84, 8035–8039. The ability of these clones to complement an opi1 mutation is shown in FIG. 3. Complementation studies reveal that the OPI1 gene, SEQ ID NO: 1, is distinct from SPO11 since plasmid p(SPO11)3, which does not complement spo11, complements opi1, and p(SPO11)9, which complements spo11, does not complement opi1. The ATR1 (Adjacent Transcript 1) gene, unlike the SPO11 gene, is not expressed during sporulation and its function is unknown. See Atcheson, C. L., DiDomenico, B., Frankman, S., Esposito, R. E. and Elder, R. T. (1987). *Proc. Natl. Acad. Sci. USA* 84, 8035–8039. Further subcloning of p(SPO11))1 eliminates the possibility that the ATR1 RNA encoded the OPI1 gene product (FIG. 3). Approximately half of the ATR1 transcription unit is deleted in p(SPO11)3 and yet this clone fully complements the opi1$^-$phenotype. Furthermore, complementation of the opi1 lesion is also observed with plasmid pJH354, demonstrating that the leftmost 1.8 kb BamHI-SstI fragment is not required for OPI1 function. Plasmid pMW12, which includes about 0.6 kb of sequence upstream of the ATR1 initiation site, does not complement the opi1$^-$phenotype. Plasmid pJH344, which does not include any of the ATR1 transcription unit, is capable of partial complementation, and the 2.0 kb XhoI-XhoI fragment (pMW10 or pMW11) which includes only a few hundred bases downstream of the ATR1 transcription start site, fully complements the opi1 lesion. Plasmids pMW10 and pMW11 contain (in opposite orientations) the smallest subclone that complements opi1 (See FIG. 3). Since either orientation of the smallest subclone is capable of complementation, the fragment most contains the entire OPI1 coding and promoter sequences. Complementation studies show that the OPI1 gene is in fact distinct from SPO11 as well as closely located gene, ATR1.

Integration of the cloned DNA, disruption of the chromosomal opi1 locus )SEQ ID NO: 1) and genetic analysis of the OPI1 insertion allele are accomplished as follows: The 2.0 kb OPI1 fragment contained on plasmids pMW10 and pMW11 is also capable of complementing an opi1 mutation in single copy. Integrating plasmids pMW14 and pMW15 (See FIG. 3 and Table 3), each containing the 2.0 kb OPI1 fragment in an opposite orientation are linearized at a unique BglII site (See FIG. 3) and used in a directed transformation of an opi1 mutant strain JHO-6D. Transformants are selected on the basis of leucine prototrophy and subsequently assayed for the opi1⁻ phenotype as described before (See FIG. 2). Southern-blot analysis of genomic DNA confirms single-copy integrants. Complementation of the opi1 lesion by a single-integrated copy of the OPI1 clone eliminates the possibility that a suppression carried in a high-copy plasmid may have been responsible for complementation by suppressing the opi1⁻ phenotype.

TABLE 3

The cloned DNA complements the Opi1⁻ phenotype and restores INO1's response to phospholipid precursors

| Yeast Genotype | INO1'lacZ Fusion | I⁺C⁺ + X-gal | I⁻C⁻ + X-gal | Excretion of Inositol |
| --- | --- | --- | --- | --- |
| OPI1 | − | white | white | − |
| opi1-1 | − | white | white | + |
| opi1-1 + pMW14 | − | white | white | − |
| opi1-1 + pMW15 | − | white | white | − |
| OPI1 | + | light blue | dark blue | − |
| opi1-1 | + | dark blue | dark blue | + |
| opi1-1 + pMW14 | + | light blue | dark blue | − |
| opi1-1 + pMW15 | + | light blue | dark blue | − |

I⁺C⁺ corresponds to 75 μM inositol and 1 mM choline, the repressed growth condition. I⁻C⁻ indicates absence of supplements, the derepressed growth condition. X-gal, 5-Bromo-4-Chloro-3-Indolyl β-D-Galactopyranoside.

Figure 5:
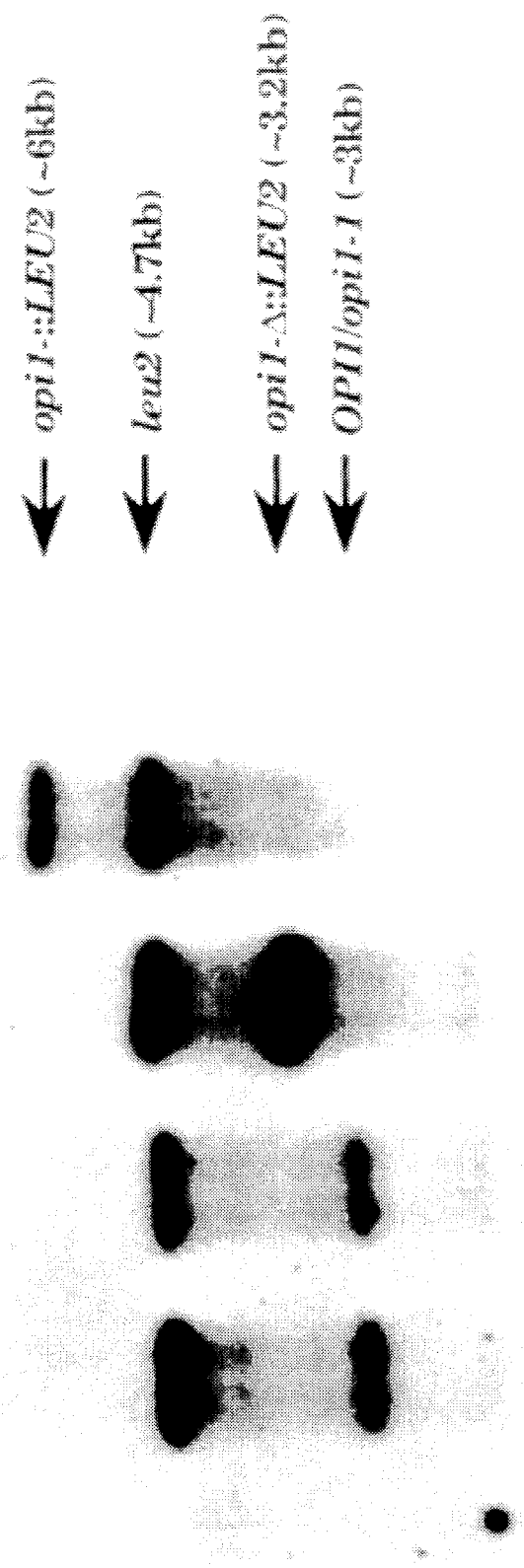
FIG. 5 illustrates Southern-blot analysis of opi1 disruption alleles. A $^{32}$P-labelled nick-translated SstI-HindIII DNA fragment from pMW20 (FIG. 4b) was used to hybridize to the Southern blot.

Insertion and deletion mutations (Table 2) are first constructed in autonomously-replicating plasmids, as described previously. Disruption of the cloned DNA is confirmed by transforming opi1 mutant strains with either plasmid pMW16 [containing an insertion of the LEU2 gene into the smallest OPI1 subclone] or pMW20 (containing a deletion of the OPI1 sequence with an insertion of the LEU2 gene). These plasmids fail to complement an opi1 mutation. To determine the phenotype of a disruption mutation at the genomic OPI1 locus, cloned DNA fragments from pMW16 and pMW20 are used in a one-step disruption transformation of a Leu2⁻ haploid strain wild-type for OPI1 (See FIGS. 4a and 4b). Leu⁺ transformants, in both cases, overproduce and excrete inositol giving a similar phenotype to existing opi1 alleles in the Opi⁻ test (See FIG. 2). Integration of the disrupted OPI1 -gene fragments at the OPI1 locus by homologous recombination is confirmed by Southern-blot analysis (See FIG. 5).

A strain containing the insertion-disruption allele opi1-::LEU2 (strain OP- 1; Table 1) is crossed with two OPI1 strains and two strains containing different opi1 alleles, opi1-1 (OPI) and opi1-12 (OPI12). Diploids are first tested for their ability to excrete inositol (See FIG. 2). Diploid strains heterozygous for the OPI1 wild-type allele and the opi1-::LEU2 allele exhibit an Opi⁺ phenotype whereas diploids produced by crossing haploid strains carrying the opi1-1 or opi1-12 alleles to strains carrying the opi1 disruption alleles have an Opi⁻ phenotype. Dissection of tetrads from the OPI1/opi1-::LEU2 diploid give the expected 2⁺:2⁻ segregation of the Opi⁺:Opi⁻ phenotype. With the exception of two tetrads out of 55, Leu⁺ co-segregates with the Opi⁻ phenotype (Table 4). Tetrads from crosses involving strains containing either an opi1-1 or opi1-12 allele with the strain carrying an opi1-::LEU2 allele show a 0⁺:4⁻ segregation pattern of Opi⁺:Opi⁻. Since the strain carrying the opi1-::LEU2 allele still contains a mutant LEU2 allele, a two-gene segregation pattern of Leu⁺:Leu⁻ is observed (Table 4). These results confirm that the inserted DNA is linked to the OPI1 locus and not to the LEU2 locus. Since a one-step gene-disruption transformation is successfully performed in a haploid strain wild-type for OPI1, this indicates that OPI1 is not an essential gene, and removal of its function is not lethal to the organism.

TABLE 4

Genetic analysis of an opi1 insertion allele confirming that the cloned gene is OPI1

| Cross | N° of tetrads dissected | Opi⁺/Opi⁻ 2:2 | Opi⁺/Opi⁻ 0:4 | Leu⁺/Leu⁻ 2:2 | Leu⁺/Leu⁻ 1:3 | Leu⁺/Leu⁻ 3:1 | Leu⁺/Leu⁻ 4:0 | Co-segregation of Opi⁻ and Leu⁺ |
| --- | --- | --- | --- | --- | --- | --- | --- | --- |
| opi1-::LEU2 his3 × WT1 leu2 | 27 | 27 | 0 | 26 | 1 | 0 | 0 | 53/54 |
| opi1-::LEU2 his3 × WT2 ade5 leu2 | 28 | 28 | 0 | 27 | 1 | 0 | 0 | 55/56 |
| opi1-::LEU2 his3 × opi1-1 lys2 | 26 | 0 | 26 | 0 | 0 | 12 | 14 | not relevant |
| opi1-::LEU2 his3 × opi1-12 lys2 | 30 | 0 | 30 | 1 | 0 | 19 | 10 | not relevant |

All other markers segregated in a 2:2 fashion.

Figure 6:
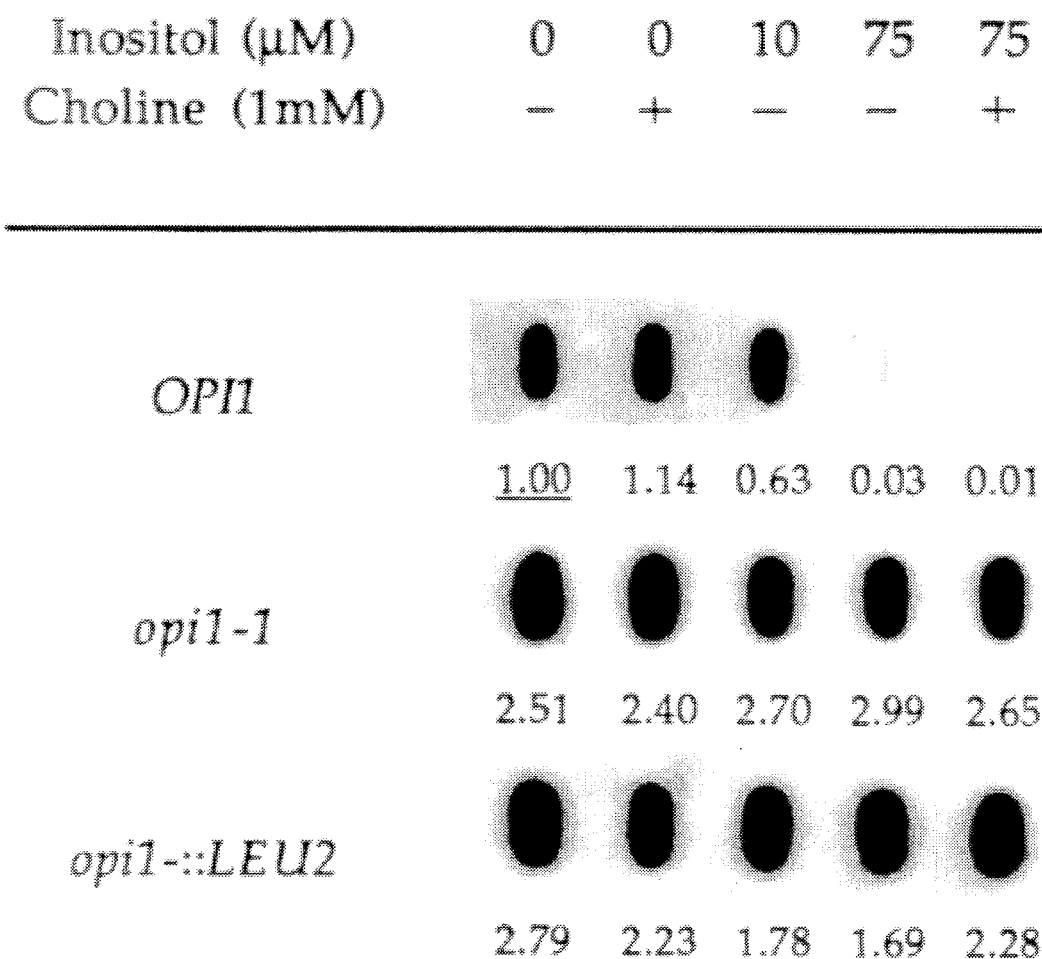
FIG. 6 illustrates slot-blot analysis of INO1 mRNA from opi1 mutant strains. Amounts of INO1 mRNA were normalized to mRNA values obtained for ribosomal protein gene TCM1 and expressed relative to wild-type derepressed levels. All values are the means of three independent determinations.

The data shows that the opi1 insertion-disruption allele expresses derepressed levels of INO1 mRNA constitutively. In order to confirm that the opi1 gene disruption strains have a phenotype similar to opi1 mutants previously isolated, levels of INO1 mRNA are analyzed in strains carrying the opi1-::LEU2 allele grown under derepressing and repressing growth conditions (See FIG. 6). Slot blots of total RNA are probed with a ³²P-labeled INO1 specific riboprobe generated from plasmid pJH320, Hirsch, J. P., and Henry S. A. (1986). *Mol. Cell. Biol.* 6, 3320–3328. The amounts of INO1 mRNA are normalized to mRNA values obtained for the ribosomal protein gene TCM1, (Fried, H. M., and Warner, J. R. (1981). *Proc. Natl. Acad. Sci. USA* 78, 238–242) to correct for differences in RNA loadings, and expressed relative to wild-type derepressed levels. Strains wild-type for the OPI1 gene regulate the level of INO1 mRNA in response to soluble phospholipid precursors (See FIG. 6). These data on expression of INO1 in wild type and opi1 strains are consistent with the data previously reported by, Hirsch, J. P., and Henry, S. A. (1986). *Mol. Cell. Biol.* 6, 3320–3328. In the strain carrying the opi1-::LEU2 allele INO1 transcription is constitutively derepressed in a manner similar to that found in the strain containing the opi1-1 allele (See FIG. 6). Both opi1 mutant strains display a two- to three-fold increase in INO1 mRNA as compared to wild-type derepressed levels. Thus the phenotype of mutants carrying the insertion-disruption allele at the OPI1 locus is identical to the phenotype of previously described opi1 mutants with regard to overproduction of inositol and INO1 expression (See FIG. 2 and FIG. 6).

It was found that the cloned DNA restores regulation of the INO1 structural gene in an opi1 background, Yeast strains carrying an integrated copy of an INO1'lacZ fusion, as described previously, (See Hirsch, J. P., Lopes, J. M., Chorgo, P. A., and Henry, S. A. (1991). *Nucl. Acids Res.*

Submitted.) were analyzed for their response to phospholipid precursors (Table 3). A strain wild-type for opil expressed β-galactosidase activity under derepressing growth conditions, as seen by a dark blue phenotype on X-gal plates. Under repressing growth conditions ($I^+C^+$) this strain has a light-blue phenotype indicating a basal/repressed level of β-galactosidase activity. The opil mutant carrying the INO1'lacZ fusion (OP-lacZ; Table 1) expresses derepressed levels of β-galactosidase, under derepressing and repressing growth conditions. The opil mutant containing an INO1'lacZ fusion, when transformed with either pMW14 or pMW15 results in the ability of the INO1 promoter to respond to repressing and derepressing growth conditions. All transformants that appeared to have restored INO1 regulation are tested for overproduction of inositol (Table 3). Complementation of the Opil⁻ phenotype coincided with the restoration of INO1's response to phospholipid precursors.

Figure 9:
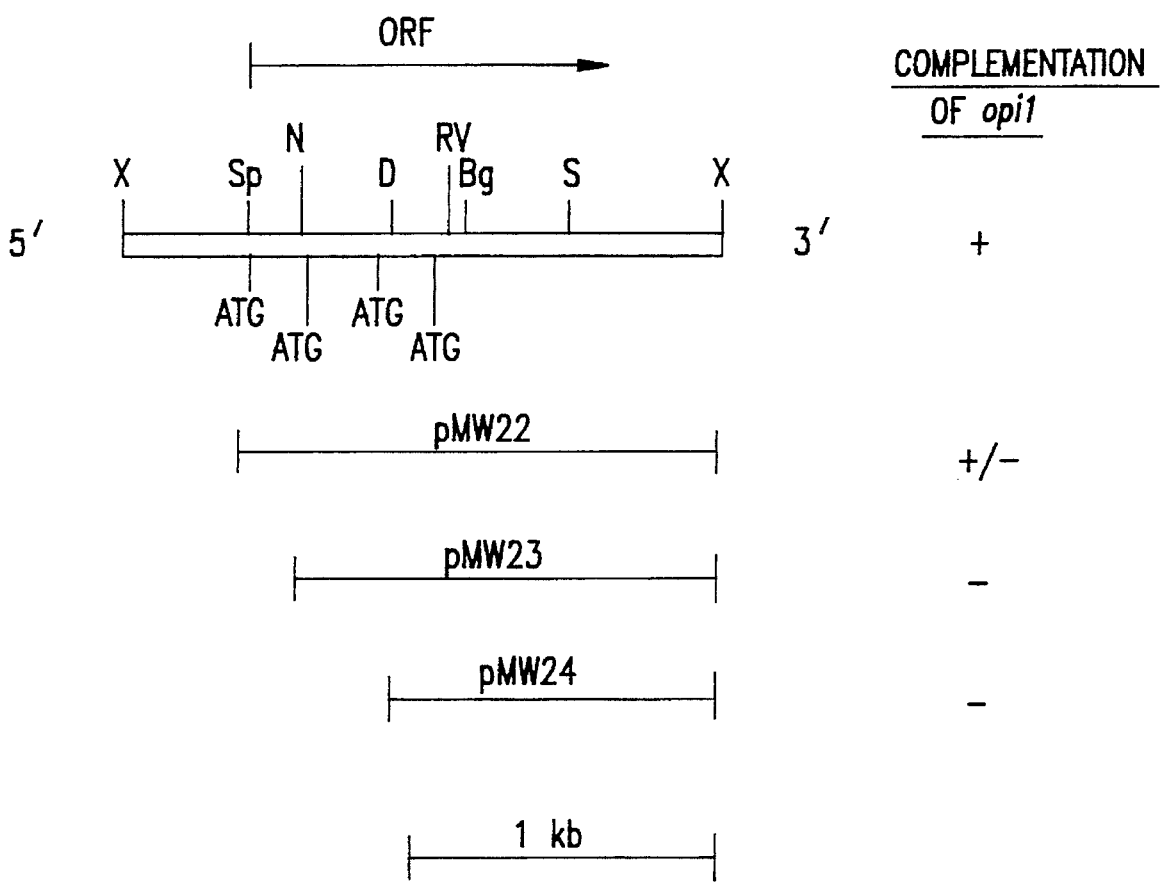
FIG. 9 illustrates deletions of the cloned opi1 gene. Ability to complement an OPI1 mutation is indicated with a (+), inability to complement is indicated with a (−) and partial complementation is indicated with a (±).

The nucleotide-sequence analysis and identification of the OPI1 coding region, SEQ ID NO: 1, are done as follows: The nucleotide sequence of the 2 kb OPI1-complementing fragment is determined using the sequencing strategy shown in FIG. 7. An open reading frame (ORF) of 1212bp is identified, starting with an ATG codon at nucleotide 439 and terminating with TAA codon at position 1650 (See FIGS. 8a–8f). Within this ORF there are three other potential translational start sites located at nucleotides 565, 829 and 1093 (See FIGS. 8a–8f). Computer analysis identified two other ORF's greater than 200bp in the opposite strand. However, these do not coincide with the position of the LEU2 gene insertion (See FIG. 4a) and are therefore eliminated from further consideration. The cloned OPI1 gene is further subcloned using unique restriction sites identified by sequence analysis (See FIG. 9). Three 5' deletions of the complementing XhoI-XhoI fragment are cloned into YEp352 to generate plasmids pMW22, pMW23 and pMW24 (Table 2). Plasmids pMW23 and pMW24 fail to complement an opil mutation because they are unable to encode the complete OPI1 protein (Opilp). Plasmid pMW22, however, partially complements the Opil⁻ phenotype, as seen by a small excretion ring in the Opi⁻ test. This clone contains 10 untranslated nucleotides upstream of the first ATG (See FIGS. 8a–8f and 9). This may suggest that the complete OPI1 gene product is translated from the sequence contained on pMW22. It is, however, possible that one of the downstream ATGs is used as the start codon, however, the data available does suggest that the ATG at nucleotide 439 is the translation initiation site for Opilp.

Strains bearing the opil mutant alleles, opil-1 (JHO-6D), opil-2 (NO80) and opil-3 (NO99), are transformed with the gapped plasmids described above. This analysis reveals that the mutations contained in all three strains lie within the same small stretch of DNA. Strains transformed with the gapped plasmids containing SpeI-NaeI, NaeI-BglII or SalI-NsiI deletions exhibit a complemented, Opi⁺, phenotype. The gaps in these plasmids do not extend past the chromosomal mutation. When strains are transformed with the BglII-SalI gapped plasmid, all retain the Opi⁻ phenotype. Failure of this construct to rescue any of the mutant alleles indicates that, in each case, the mutation must lie between the BglII and the SalI restriction sites of the OPI1 locus. Sequencing of EcoRV-SalI fragments from re-isolated gapped plasmids (See FIG. 3) identifies nonsense mutations in each of the three alleles, all located within the first polyglutamine stretch of amino acid residues. Alleles opil-3 and opil-2 have a "TAA" codon located at nucleotide 1294 and 1312 respectively, whereas strain opil-1 has a "TAG" codon at nucleotide 1315 (See FIGS. 8a–8f).

The Opil protein is analyzed as follows: Translation of the OPI1 ORF predicts a protein (Opilp) composed of 404 amino acids (SEQ ID NO: 2) (See FIGS. 8a–8f) with a molecular weight of 40,036. Opilp is a fairly acidic protein having an isoelectric point of 4.77. The codon bias produced for Opilp using the method of Bennetzen, J. L., and Hall, B. D. (1982). *J. Biol. Chem.* 257, 3026–3031, was 0.089, indicating that the OPI1 gene product is a low-abundance protein Bennetzen, J. L., and Hall, B. D. (1982). *J. Biol. Chem.* 257, 3026–3031; Sharp, P., Tuhoy, T., and Mosurski, K. (1986). *Nucl. Acids Res.* 14, 5125–5143. This is consistent with the fact that Opilp is a regulatory protein. Hydropathicity analysis, Kyte, J., and Doolittle, K. F. (1982). *J. Mol. Biol.* 157, 105–132, of Opilp indicates no substantial hydrophobic regions suggesting that there are no membrane spanning regions. A heptad repeat of leucine residues (leucine zipper) is identified in the amino-acid sequence, starting at nucleotide 853 (See FIGS. 8a–8f).

In a structural analysis of several proteins that are involved in gene regulation, Landschulz, W. H., Johnson, P. F., and McKnight, S. L. (1988). *Science* 240, 1759–1764, identified a leucine zipper encoded in the yeast transcriptional regulatory gene, GCN4, and the mammalian enhancer binding protein, C/EBP, as well as the proto-oncogene products belonging to the Jun, Fos, and Myc family of nuclear transforming proteins. This structure forms a stable α-helix whereby the leucines, repeated every seventh residue, form a hydrophobic spine down one face of the helix. The dimerization of monomer is stabilized by hydrophobic interactions between closely opposed α-helical leucine repeats, Landschulz, W. H., Johnson, P. F., and McKnight, S. L. (1988). *Science* 240, 1759–1764. The formation of these protein complexes is involved in the juxtapositioning of basic domains, or other DNA-binding domains, that facilitate binding of the protein to DNA. When represented in the form of helical structure the Opilp leucine zipper region exhibits amphipathicity that is consistent with many of the aforementioned DNA-binding proteins. The leucine residues of the zipper align down one face every second turn of the α-helix, while immediately opposite is a preponderance of amino-acid residues having either charged or uncharged polar side-chains. In addition, there are more hydrophobic residues that lie adjacent to the leucine residues at three out of four positions. It is believed that these adjacently positioned hydrophobic residues may add to the stability of hetero- or homo-dimers ill the form of a coiled coil. (See Gentz, R., Rauscher, F., J., III, Abate, C., and Curran, T. (1989). *Science* 243, 1695–1699; Landschulz, W. H., Johnson, P. F., and McKnight, S. L. (1989). *Science* 243, 1681–1688; O'Shea, E. K., Rutkowski, R., and Kim, P. S. (1989a). *Science* 243, 538–542; O'Shea, R. K., Rutkowski, R., Stafford, W., F., III, and Kim, P. S. (1989b). *Science* 245, 646–648; Ransone, L. J., Visvader, J., Sassone-Corsi, P., and Verma, I. M. (1989). *Genes Devel.* 3,770–781; Smeal, T., Angel, P., Meek, J., and Karin, M. (1989). *Genes Devel.* 2091–2100).

Immediately $NH_2$-terminal to the Opilp leucine zipper is a 30 amino-acid residue region that contains a net basic charge. The basic domain is directly involved in protein-DNA binding and, together, the leucine zipper and basic domain are implicated as having a role in some DNA-binding proteins that regulate transcription. (See Landschulz, W. H., Johnson, P. F., and McKnight, S. L. (1988). *Science* 240,1759–1764; Landschulz, W. H., Johnson, P. F., and McKnight, S. L. (1989). *Science* 243, 1681–1688; Brendel, V., and Karlin, S. (1989). *Proc. Natl. Acad. Sci. USA* 86, 5698–5702; Kouzarides, T., and Ziff, E. (1989).

*Nature* 340, 568–571; Vinson, C. R., Sigler, P. B., and McKnight, S. L. (1989). *Science* 246, 911–916).

Based on the identification of cis-acting regulatory elements in the 5' promoter region on INO1, Hirsch, J. P., Lopes, J. M., Chorgo, P. A., and Henry, S. A. (1991). *Nucl. Acids Res.*, Submitted, has employed DNA-binding/mobility-shift assays along with oligonucleotide competition experiments to assess the possible interaction of DNA-binding proteins with the INO1 promoter. Using protein extracts from cells wild-type for OPI1 as well as extracts from strains carrying the disruption alleles, an OPI1-dependent protein-DNA complex has been identified. When these studies are repeated using extracts from a strain carrying the opi1-1 allele transformed with the cloned OPI1 gene, the protein-DNA complex reappears. That Opi1p contains a well defined leucine zipper and associated basic domain makes it a DNA-binding repressor protein that binds directly to the INO1 promoter, and the promoter of other structural genes involved in the phospholipid biosynthetic pathway. Opi1p may either dimerize with itself in the form of a coiled coil, similar to the yeast transcriptional activator encoded by GCN4, Kouzarides, T., and Ziff, E. (1989). *Nature* 340, 568–571; O'Shea, E. K., Rutkowski, R., and Kim, P. S. (1989). *Science* 243, 538–542, or complexes with another protein to form a heterodimer, similar to the c-jun and c-fos proto-oncogene products, Kouzarides, T., and Ziff, E. (1989). *Nature* 340, 568–571; Ransone, L. J., Visvader, J., Sassone-Corsi, P., and Verma, I. M. (1989). *Genes Devel.* 3, 770–781.

Two polyglutamine-residue stretches are also found in the translated OPI1 sequence, SEQ ID NO: 2 starting at nucleotides 1294 and 1567 (See FIGS. 8a–8f). One consists of 21 glutamine resides with two intervening leucine doublets, and a smaller one of 9 glutamine residues is interrupted by a single tyrosine and arginine residue. Searching the nucleotide- and protein-sequence databases identified several genes with similarities to OPI1. However, this was due in large to the presence of sequences encoding polyglutamine residues. It is striking that glutamine-rich regions and polyglutamine tracts are being reported in an increasing number of predicted yeast proteins that have regulatory functions. When Opi1p is analyzed using the FLEXPRO program in PC/GENE (version 6.01) the polyglutamine tracts are predicted to confer flexibility to the protein. This property may be involved in the orientation of binding domains to specific sites on DNA and/or other DNA-binding proteins, Bohmann, D., Bos, T. J.,. Admon, A., Nishimura, T., Vogt, P. K., and Tijan, R. (1987). *Science* 238, 1386–1392; Brendel, V., and Karlin, S. (1989). *Proc. Natl. Acad. Sci. USA* 86, 5698–5702. The opi1 nonsense mutations and the opi1 insertion-disruption mutation all truncate Opi1p, removing the polyglutamine tracts. This causes the disappearance of an OPI1-dependent DNA-protein complex involving the INO1 promoter possibly implicating a role for this structural motif in DNA binding. This interpretation is further supported by the fact that plasmid pJH344 (See FIG. 3), which contains the first long stretch of polyglutamine-residues but has the most carboxy-terminal stretch deleted, partially complemented an opi1 mutation.

The nucleotide sequence of OPI1 (SEQ ID NO: 1) has identified a gene product that has properties consistent with its predicted role as a DNA-binding protein. The finding that Opi1p possesses structural motifs, such as a leucine zipper and polyglutamine tracts (See FIGS. 8a–8f), that are found in a wide variety of DNA-binding proteins is a particularly significant one.

With respect to the preferred embodiment of the multiple copies of the INO1 gene, the following methods are used to construct diploid opi1⁻ disruption strains containing multiple insertions of the gene, INO1, encoding for inositol 1-phosphate synthase:

1. Haploid yeast strains, opi1-:LEU2, leu2, or LEU2, his3,ura3, MATa and opi1-::LEU2, leu2, or LEU2, his3, ura3, MAT, capable of receiving integrating plasmids containing the cloned INO1 gene are constructed.

2. The fully-regulated INO1 gene fragment [SstI-HindIII from pJH318; Hirsch, J. (1987). Ph.D. Thesis, Albert Einstein College of Medicine, Bronx, N.Y.] is subcloned into the integrating vector YIp 352 [Hill J. E., Myers, A. M., Koerner, T. J. and Tzagoloff, A. (1986). Yeast 2, 163–167].

3. Yeast transformations involving the two above mentioned opi1-::LEU2 haploid strains and the integrating plasmid containing INO1 are performed using the methods described above. Integrating plasmids are directed at the mutated URA3 locus in each case using linearized plasmid cut internal to the URA3 marker. Transformants are selected on plates lacking uracil (URA⁻ plates). Uracil prototrophs are checked again for correct selectable markers, mating type and Opi⁻ phenotype as described previously.

4. Southern-blot analysis of opi1-::LEU2 transformants confirming integration of plasmids containing the INO1 gene are prepared as described in methods to follow.

5. Transformants of opposite mating type, containing more than one copy of the INO1 gene as identified by Southern-blot analysis, are mated and diploids (containing six or more copies of INO1) selected using a micromanipulator. Diploids are tested for the Opi⁻ phenotype as described above.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A genetically engineered yeast cell of the genus Saccharomyces having multiple integrated copies of an INO1 gene expression construct, and wherein all copies of the OPI1 gene (SEQ ID NO: 1) are replaced, resulting in all copies of the OPI1 gene (SEQ ID NO: 1) being deleted.

2. The yeast cell of claim 1 wherein the OPI1 gene encodes the negative regulator Opi1p.

3. The yeast cell of claim 1 wherein said yeast cell is of the type *Saccharomyces cerevisiae*.

4. The yeast cell of claim 1 wherein the OPI1 gene has the nucleotide and amino acid sequence as shown in FIGS. 8a–8f (SEQ ID NOS:1-2).

5. The yeast cell of claim 2 wherein the Opi1p consists of 404 amino acid residues (SEQ ID NO: 2) and has a molecular weight of 40,036.

6. The yeast cell of claim 5 wherein the Opi1p contains polyglutamine tracts and a leucine zipper.

7. The yeast cell of claim 1 wherein there are 3–6 copies of said INO1 gene expression construct therein.

8. A method of making a genetically engineered yeast cell of the genus Saccharomyces, comprising the steps of:
  a. replacing all the copies of the OPI1 gene (SEQ ID NO: 1) such that all copies of the OPI1 gene (SEQ ID NO: 1) are deleted in said yeast cell; and
  b. transforming said yeast cell with a DNA construct wherein integration of multiple copies of an INO1 gene expression construct results.

9. The method of claim 8 wherein the yeast cell is of the type *Saccharomyces cerevisiae*.

10. A method for the enhanced production of inositol, inositol-containing metabolites or phospholipids in a genetically engineered yeast cell of the genus Saccharomyces, comprising the steps of:
  a. replacing all the copies of the OPI1 gene (SEQ ID NO:1) such that all copies of the OPI1 gene (SEQ ID NO:1) are deleted in said yeast cell;
  b. transforming said yeast cell with a DNA construct wherein the integration of multiple copies of an INO1 gene expression construct results;

c. culturing said transformed yeast cell so as to allow for inositol, inositol-containing metabolites or phospholipids to be produced; and d. recovering said inositol, inositol-containing metabolites or phospholipids.

11. The method of claim 10, wherein said yeast cell is of the type *Saccharomyces cerevisiae.*

12. The method of claim 10 wherein the inositol, inositol-containing metabolites or phospholipids includes myo-inositol or inositol-1-phosphate.

13. The method of claim 10 wherein the OPI1 gene encodes the negative regulator Opi1p.

14. The method of claim 10 wherein the OPI1 gene has the nucleotide and amino acid sequence as shown in FIGS. 8a–8f (SEQ ID NOS:1–2).

15. The method of claim 14 wherein the Opi1p consists of 404 amino acid residues (SEQ ID NO: 2) and has a molecular weight of 40,036.

16. The method of claim 15 wherein the Opi1p contains polyglutamine tracts and a leucine zipper.

* * * * *